United States Patent
Katagiri et al.

(10) Patent No.: US 9,063,157 B2
(45) Date of Patent: *Jun. 23, 2015

(54) METHOD FOR EVALUATING SKIN CONDITION USING SQUAMOUS CELL CARCINOMA ANTIGEN AS MARKER

(75) Inventors: Chika Katagiri, Yokohama (JP); Jotaro Nakanishi, Yokohama (JP); Toshihiko Hibino, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 609 days.

This patent is subject to a terminal disclaimer.

(21) Appl. No.: 11/886,488

(22) PCT Filed: Mar. 17, 2006

(86) PCT No.: PCT/JP2006/306043
§ 371 (c)(1),
(2), (4) Date: Sep. 17, 2007

(87) PCT Pub. No.: WO2006/098523
PCT Pub. Date: Sep. 21, 2006

(65) Prior Publication Data
US 2009/0233319 A1    Sep. 17, 2009

(30) Foreign Application Priority Data
Mar. 18, 2005  (JP) .................. 2005-080533

(51) Int. Cl.
*C12Q 1/00*   (2006.01)
*G01N 33/53*  (2006.01)
*G01N 33/68*  (2006.01)
G01N 33/50   (2006.01)

(52) U.S. Cl.
CPC ........ *G01N 33/6881* (2013.01); *G01N 2800/24* (2013.01); *G01N 2800/20* (2013.01); *G01N 2800/205* (2013.01); *G01N 33/5005* (2013.01); *G01N 33/53* (2013.01); *G01N 33/5091* (2013.01); *G01N 2800/202* (2013.01); *G01N 2800/40* (2013.01)

(58) Field of Classification Search
CPC .......... G01N 33/6881; G01N 2800/20; G01N 2800/24; G01N 2800/202; G01N 2800/205; G01N 2800/203; G01N 33/5005; G01N 33/53; C12Q 2600/158
See application file for complete search history.

(56) References Cited

U.S. PATENT DOCUMENTS

2005/0215509 A1  9/2005  Katagirl et al.
2007/0160545 A1  7/2007  Katagiri et al.

FOREIGN PATENT DOCUMENTS

JP   2005-272343 A   10/2005
WO   WO 01/74851      10/2001
WO   WO 02/44736       6/2002

OTHER PUBLICATIONS

Rowe et al., California Medicine, 1959, 91(6): 341-343.*
Cataltepe et al., J. Histochem. Cytochem., 2000, 48(1): 113-122.*
Brown, BMJ: British Medical Journal, 2006, 332 (7541): 584-588.*
Yamane et al., Int Arch Allergy Immunol, 2009, 150:89-101.*
Campbell et al., "Squamous cell carcinoma antigen in patients with cutaneous disorders", *J Am Acad Dermatol*, 22:639-642 (1990).
European Search Report, Application No. 06729991.7, Sep. 8, 2008.
Eckhart et al., "Terminal Differentiation of Human Keratinocytes and Stratum Corneum Formation is Associated with Caspase-14 Activation," *The Journal of Investigative Dermatology*, vol. 115:1148-1151 (2000).
Eckhart et al., "Caspase-14: Analysis of Gene Structure and mRNA Expression during Keratinocyte Differentiation," *Biochemical and Biophysical Research Communications*, vol. 277:655-659 (2000).
Gagliardini et al., "Prevention of Vertebrate Neuronal Death by the crmA Gene," *Science*, vol. 263:826-828 (1994).
Hopsu-Havu et al., "Separation of cysteine proteinase inhibitors from psoriatic scale," *British Journal of Dermatology*, vol. 109:77-85 (1983).
Hu et al., "Caspase-14 Is a Novel Developmentally Regulated Protease," *The Journal of Biological Chemistry*, vol. 273:29648-29653 (1998).
Hurle et al., "Elastin exhibits a distinctive temporal and spatial pattern of distribution in the developing chick limb in association with the establishment of the cartilaginous skeleton," *Journal of Cell Science*, vol. 107:2623-2634 (1994).
Kato et al., "Radioimmunoassay for Tumor Antigen of Human Cervical Squamous Cell Carcinoma," *Cancer*, vol. 40:1621-1628 (1977).
Lippens et al., "Epidermal differentiation does not involve the pro-apoptotic executioner caspases, but is associated with caspase-14 induction and processing," *Cell Death and Differentiation*, vol. 7:1218-1224 (2000).
Lunstrum et al., "Large Complex Globular Domains of Type VII Procollagen Contribute to the Structure of Anchoring Fibrils," *The Journal of Biological Chemistry*, vol. 261:9042-9048 (1986).
Mikolajczyk et al., "Activation and Substrate Specificity of Caspase-14," *Biochemistry*, vol. 43:10560-10569 (2004).
Mino et al., "Availability of Tumor-Antigen 4 as a Marker of Squamous Cell Carcinoma of the Lung and Other Organs," *Cancer*, vol. 62:730-734 (1988).
Nagata, "Apoptotic DNA Fragmentation," *Experimental Cell Research*, vol. 256:12-18 (2000).
Sakurai et al., "Occurrence of patchy parakeratosis in normal-appearing skin in patients with active atopic dermatitis and in patients with healed atopic dermatitis: a cause of impaired barrier function of the atopic skin," *Journal of Dermatological Science*, vol. 30:37-42 (2002).

*Primary Examiner* — Hong Sang
(74) *Attorney, Agent, or Firm* — Foley & Lardner LLP

(57) ABSTRACT

The invention provides a method for evaluating skin condition using squamous cell carcinoma antigen (SCCA) expression in skin stratum corneum cells as a marker.

8 Claims, 15 Drawing Sheets

(56) References Cited

OTHER PUBLICATIONS

Schick et al., "Squamous Cell Carcinoma Antigen 2 is a Novel Serpin that Inhibits the Chymotrypsin-like Proteinases Cathepsin G and Mast Cell Chymase," *The Journal of Biological Chemistry*, vol. 272:1849-1855 (1997).

Srinivasula et al., "A conserved XIAP-interaction motif in caspase-9 and Smac/DIABLO regulates caspase activity and apoptosis," *Nature*, vol. 410:112-116 (2001).

Takahashi et al., "Partial Purification and Characterization of Two Distinct Types of Caspases from Human Epidermis," *The Journal of Investigative Dermatology*, vol. 111:367-372 (1998).

Takeda et al., "Overexpression of Serpin Squamous Cell Carcinoma Antigens in Psoriatic Skin," *The Journal of Investigative Dermatology*, vol. 118:147-154 (2002).

Takeda et al., "Aberrant Expression of Serpin Squamous Cell Carcinoma Antigen 2 in Human Tumor Tissues and Cell Lines: Evidence of Protection from Tumor Necrosis Factor-Mediated Apoptosis," *Biol. Chem.*, vol. 383:1231-1236 (2002).

Tang et al., "Cleavage of DFF-45/ICAD by Multiple Caspases Is Essential for Its Function during Apoptosis," *The Journal of Biological Chemistry*, vol. 273:28549-28552 (1998).

Valdés et al., "Atopic dermatitis. Findings of skin biopsies," *Allergologia et Immunopathologia*, vol. 18:321-324 (1990).

Van de Craen et al., "Identification of a new caspase homologue: caspase-14," *Cell Death and Differentiation*, vol. 5:838-846 (1998).

Chien et al., "Processing of Native Caspase-14 Occurs at an Atypical Cleavage Site in Normal Epidermal Differentiation," *Biochemical and Biophysical Research Communications*, vol. 296:911-917 (2002).

Weil et al., "Caspase Activation in the Terminal Differentiation of Human Epidermal Keratinocytes," *Current Biology*, vol. 9:361-364 (1999).

Takeda, Atsushi, et al., "Overexpression of Serpin Squamous Cell in Psoriatic Skin," *Journal of Investigative Dermatology*, Jan. 2002, pp. 147-154, vol. 118, No. 1

Rivas, Miriam V., et al., Identificatin of Aberrantly Regulated Genes in Diseased Skin Using the cDNA Differential Display Technique, *Journal of Inestigative Dermatology*, Feb. 1997, pp. 188-194, vol. 108, No. 2.

Proceedings of Alliance Meeting of 52nd Japan Society of Laboratory Medicine Assembly and 45th Japanese Society of Clinical Chemistry Annual Meeting and Clinical Test Medical Association, "Discovery of Novel Clinical Marker by Means of Microarray 1—Significance of Squamous Cell Carcinoma Antigen as Clinical Marker," 2005, S1-3, p. 23 (see concise explanation of relevance in transmittal letter).

\* cited by examiner

Fig.1
A
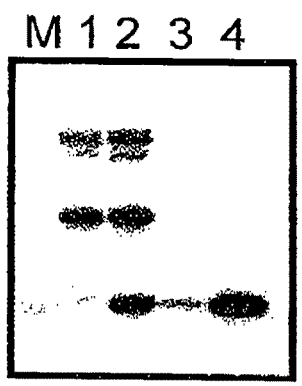
H99 ANTIBODY
B
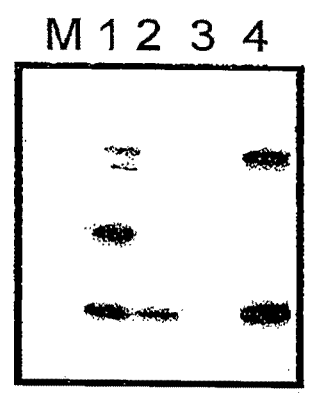
h14D¹⁴⁶ ANTIBODY

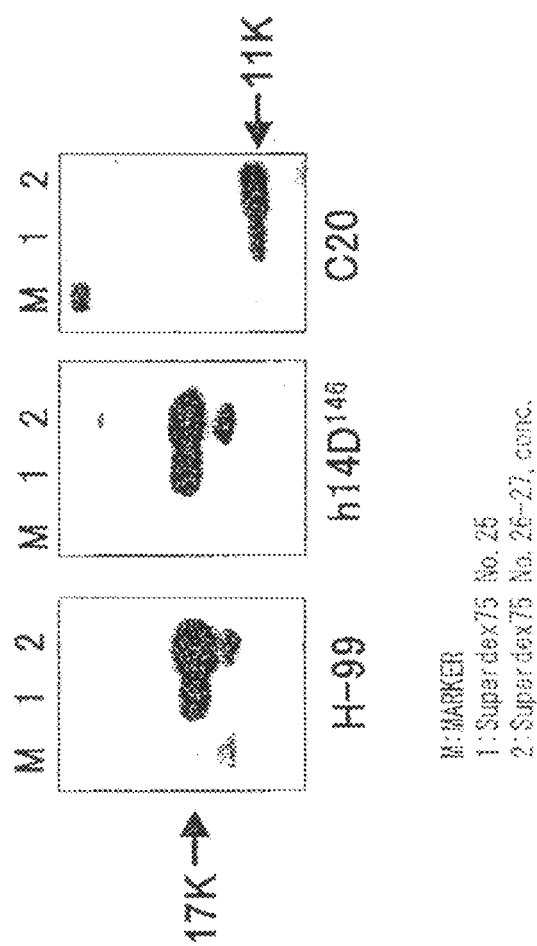
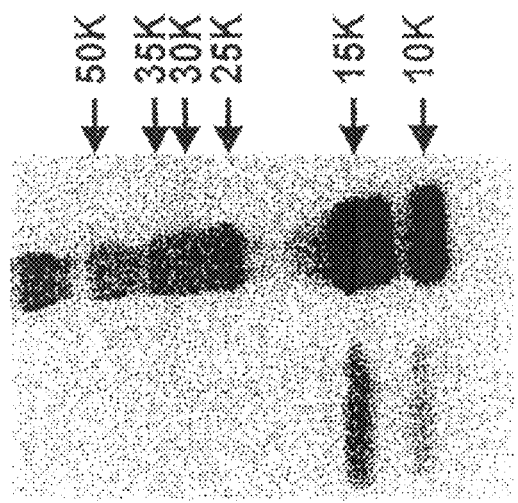
Fig. 2

Fig. 4
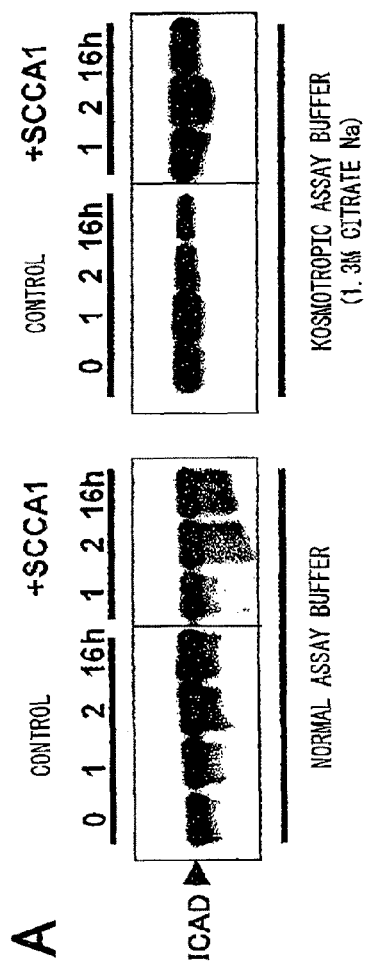
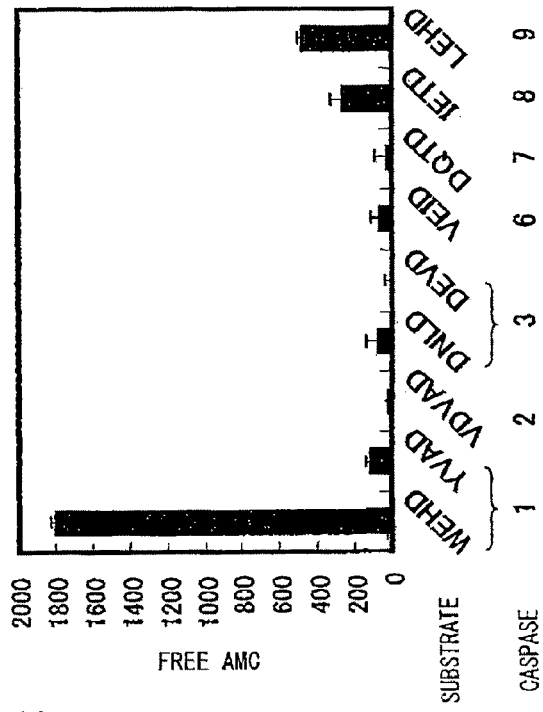
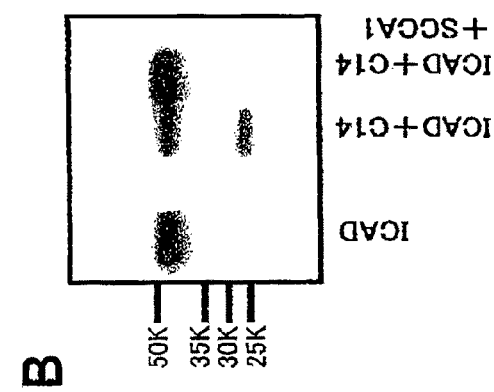

METHOD FOR EVALUATING SKIN CONDITION USING SQUAMOUS CELL CARCINOMA ANTIGEN AS MARKER

TECHNICAL FIELD

The present invention provides a method for evaluating the condition of skin using cellular squamous cell carcinoma antigen (hereinafter abbreviated as "SCCA") as a marker.

BACKGROUND ART

Normal cornification of skin causes a phenomenon known as "denucleation", whereby the nuclei of keratinocytes disappear. Epidermal keratinocytes proliferate in the basal layers, and migrate to the upper layers where they mature into the stratum corneum. However, in rough skin that has not undergone normal cornification, as a result of skin diseases such as psoriasis or atopic dermatitis, the nuclei of the cornified cells remains in a undigested state, whereby the cornified cells are found in the stratum corneum in an immature state in which nuclei is retained. This condition is known as "parakeratosis". Although the phenomenon of parakeratosis has long been recognized, the mechanism by which parakeratosis occurs, and the biochemical markers for it, have been unknown.

Squamous cell carcinoma antigen (SCCA), an antigen extracted from squamous carcinoma cells, is found at high concentration in blood from patients suffering from squamous cell carcinoma of the uterine cervix, lungs, esophagus or skin, and it is commonly used for diagnosis of squamous cell carcinoma (Kato H. et al. Cancer 40:1621-1628 (1977); Mino N. et al. Cancer 62: 730-734 (1988)). In particular, SCCA blood level positively correlates with squamous cell carcinoma progression stage, malignancy and tumor size, and it is an especially effective cancer marker not only for early detection of cancer but also for evaluating treatment effects and diagnosing the risk of recurrence.

SCCA is also known to be overexpressed in the upper layer of psoriatic epidermis (Takeda A. et al, J. Invest. Dermatol. 118(1): 147-154 (2002)). Psoriasis is a type of skin disease that can take the form of chronic, relapsing inflammatory parakeratosis characterized by abnormal proliferation and differentiation of epidermal cells and infiltration of inflammatory cells. Onset of psoriasis is attributed both to genetic factors and to various environmental factors (Hopsu-Havu et al. British Journal of Dermatology 109: 77-85 (1983)).

There are two kinds of genes, i.e., SCCA-1 and SCCA-2, situated in tandem on chromosome 18q21.3 which code for SCCA. The proteins SCCA-1 and SCCA-2 encoded by these genes are of approximately 45,000 in molecular weight, and exhibit high homology of 95% on the nucleic acid level. The SCCA proteins belong to the ovalbumin-serine protease inhibitor (ov-serpin) family. The ov-serpin family has unique characteristics among the serpin superfamily. Serpins are generally secreted and act extracellularly, but ov-serpins are protease inhibitors that act primarily intracellularly.

SCCA-1 is a papain-like cysteine protease inhibitor while SCCA-2 is a chymotrypsin-like serine protease inhibitor, and despite their high homology, their differing amino acid sequences at the reactive site are responsible for producing different behavior (Schick et al. J. Biol. Chem. 272(3): 1849-55 (1997)). It has been known that SCCA-1 and SCCA-2 are highly expressed in diseases such as psoriasis or by UV irradiation, but their association with skin condition has not been elucidated.

DISCLOSURE OF THE INVENTION

As a result of research aimed at elucidating the physiological mechanism of SCCA in the epidermis, the present inventors have discovered that SCCA expression is specifically promoted in parakeratotic skin such as psoriasis, and that SCCA is a factor involved in rough skin conditions, including parakeratosis. It was therefore conjectured that SCCA expression can serve as a marker for such skin conditions, and the invention has thus been completed.

The present invention provides a method for evaluating skin condition using squamous cell carcinoma antigen (SCCA), specifically expression of SCCA-1 and/or SCCA-2, and especially SCCA-1 in skin stratum corneum cells as a marker. The SCCA expression is preferably measured by enzyme-linked immunosorbent assay (ELISA) using SCCA-specific antibodies. According to a more preferred mode, a sample of the skin stratum corneum is taken by tape stripping.

The method of the invention allows skin conditions such as roughening and parakeratosis to be judged on the biochemical level. The skin conditions to be judged by the method of the invention may include various types of conditions including roughness, skin aging due to ultraviolet irradiation exposure, for example, and skin dryness due to reduced skin moisture retention ability with loss of skin barrier function, parakeratosis caused by psoriasis or atopic dermatitis, and skin roughening caused by pollen hypersensitivity.

BRIEF DESCRIPTION OF THE DRAWINGS

FIGS. 1A-1B show Western blot analysis for a skin extract. H-99 antibody (FIG. 1A) and h14D$^{146}$ antibody (FIG. 1B) were used for immunoblot analysis of zymogen and active caspase-14. There were used 10 μg (lanes 1, 2 and 4) and 1 μg (lane 3) of total skin extract, skin equivalent extract and keratinocyte extract.

FIG. 2 shows analysis of purified caspase-14. (A) Following SDS-polyacrylamide gel electrophoresis, fraction No. 25 obtained from Superdex 75 chromatography was applied to a PVDF membrane and stained with Coomassie Brilliant Blue. Two protein bands of 17 KDa and 11 KDa were observed. (B) Western blotting analysis using H-99, h14D$^{146}$ and C20 antibody. The 17 KDa band was positive for both H99 antibody and h14D$^{146}$ antibody, while the 11 KDa band was recognized by C20 antibody. M: Marker; 1: Superdex 75 No. 25; 2: Superdex 75 No. 26-27, comc.

FIG. 4 (A) shows the cleavage activity of purified caspase-14 for ICAD. (B) shows Western blotting analysis using FL331 antibody. Identified were 33 KDa and 27 KDa cleavage products. Incubation using 10 μM of SCCA-1 completely inhibited ICAD cleavage. ICAD decomposition was observed only in the presence of a kosmotropic salt. Western blotting analysis using an amino terminus-specific antibody revealed disappearance of intact ICAD molecules during prolonged incubation with caspase-14. Addition of SCCA-1 to the mixture resulted in inhibition of ICAD decomposition, and no change was detected even after 16 hours of incubation (B). (C) shows the results of examining hydrolytic activity on synthetic caspase substrate, in the presence of a kosmotropic salt.

BEST MODE FOR CARRYING OUT THE INVENTION

Figure 3:
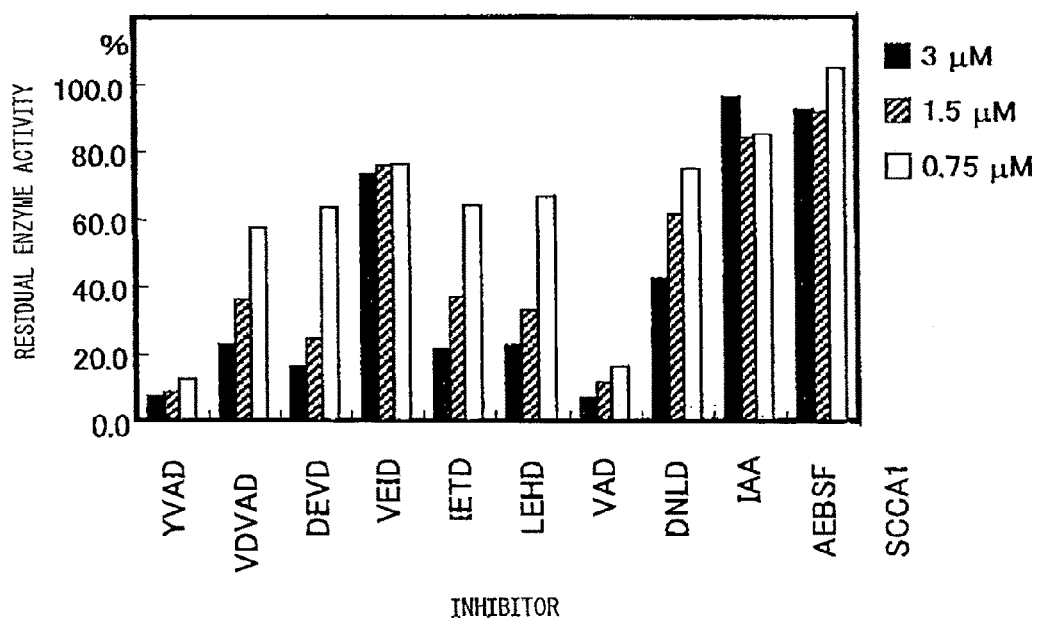
FIG. 3 shows the effect of various synthesis inhibitors on purified caspase-14. Currently, 15 types of human caspases are known, but caspase-14 was incubated together with various peptide inhibitors for caspases (YVAD (SEQ ID NO:3), VDVAD (SEQ ID NO:4), DEVD (SEQ ID NO:5), VEID (SEQ ID NO:6), IETD (SEQ ID NO:7), LEHD (SEQ ID NO:8), DNLD (SEQ ID NO:9)), class-specific inhibitors for cysteine proteinases (IAA) or serine proteinases (AEBSF). WEHD-MCA (SEQ ID NO:10) was used as substrate in the presence of 1.3 M sodium citrate and 5 mM DTT, and the residual enzyme activity was measured. The tested enzyme concentrations were 5, 2.5 and 1.25 μM. The values were represented as mean values for multiple assays.

As mentioned above, SCCA is a protein with a molecular weight of approximately 45,000 whose expression is accelerated in psoriasis or UV-irradiated skin. The amino acid sequences of SCCA-1 and SCCA-2, and the nucleic acid sequences coding therefor, are listed in Takeda A et al. J. Invest. Dermatol. 118, 147-154 (2002) (ibid).

SCCA expression can be measured according to the present invention either quantitatively or qualitatively, by any desired method capable of measuring SCCA. Specifically, there may be mentioned immunoassay methods utilizing SCCA-specific antibodies, such as ELISA using an enzyme label, RIA using a radioactive label, immunoturbidimetry, Western blotting methods, latex agglutination methods, hemagglutination methods, and the like. There may also be mentioned immunoassay methods such as competitive and sandwich assays. In addition, SCCA expression can be measured based on the level of intracellular expression of the gene coding for it. In this case, the SCCA expression is preferably determined by measuring the intracellular level of mRNA coding for SCCA. The mRNA extraction and quantitative or qualitative detection may be accomplished by methods known in the field, such as PCR, 3SR, NASBA and TMA. SCCA expression may also be qualitatively determined by in situ hybridization or by methods measuring its bioactivity.

The skin stratum corneum specimen to be used as a sample may be obtained by any desired method, but tape stripping is preferred from the viewpoint of convenience. Tape stripping is a method wherein an adhesive tape strip is applied to the skin surface and peeled off to attach a portion of the skin stratum corneum to the peeled adhesive tape for use as the stratum corneum sample. Using the tape stripping method allows measurement of SCCA expression in the stratum corneum using a single piece of tape, as a noninvasive method of evaluating roughening or parakeratosis based on SCCA as the marker. A preferred tape stripping method is one in which the skin surface is first cleaned with ethanol or the like to remove sebum and dirt, an adhesive tape strip cut to a suitable size (for example, 2×5 cm) is lightly placed over the skin surface and force is applied equally onto the entire tape to flatten it, after which the adhesive tape is peeled off with a uniform force. The adhesive tape may be commercially available cellophane tape, and for example, it may be Scotch Superstrength Mailing Tape (3 M), cellophane tape (Cellotape™; Nichiban Co., Ltd.) or the like. The SCCA in the skin stratum corneum sample attached to the adhesive tape may be isolated and extracted from the tape by immersing the tape strip in an appropriate extraction solution such as Tris-buffer (pH 8.0) (0.1 M Tris-HCl, 0.14 M NaCl, 0.1% Tween-20) for extraction of the stratum corneum.

According to a preferred mode of the invention, the SCCA is assayed by an immunoassay method such as ELISA. The SCCA-specific antibody used for ELISA may be a monoclonal antibody or polyclonal antibody. Methods for preparing monoclonal antibodies and polyclonal antibodies are known to those skilled in the art and are described, for example, in Lunstrum et el., J. Biol. Chem., 261: 9042-9048 (1986) and Hurle et al. J Cell Science, 107: 2623-2634 (1994).

A sandwich immunoassay is especially preferred as the method for the invention. The sandwich immunoassay method is carried out in the following manner, for example.

One of two specific antibodies for SCCA is immobilized on a carrier as the primary antibody. The carrier is preferably a solid carrier, and for example, the solid carrier may be any one ordinarily used for immunoassay methods, such as a polymer carrier made of styrene or polystyrene formed to the desired shape and size, or a reactor made of such appropriate materials, such as the inner walls of the wells of an ELISA plate, may be mentioned as an example.

The immobilization of the primary antibody on the carrier may be accomplished by any ordinary method, and for example, the primary antibody may be immobilized via dissolution in a buffering solution such as a phosphate-buffered saline (PBS), borate buffer or the like for adsorption on the carrier. Also, an antibody or other protein to be bound to the primary antibody, such as protein C, for example, may first be immobilized on a carrier and then contacted with the primary antibody. In order to inhibit non-specific binding, the primary antibody-immobilizing carrier is preferably blocked with a blocking agent, for example by addition of PBS-BSA or a commercially available blocking agent such as BLOCKACE (Dainippon Pharmaceutical Co., Ltd.), with incubation at about 4-40° C. and preferably 20-37° C. for a period from 5 minutes to several days, preferably 10 minutes to 24 hours and more preferably 10 minutes to 3 hours.

The other antibody of the two different SCCA-specific antibodies is labeled for use as the secondary antibody. The labeling may be enzyme labeling, radioactive labeling, fluorescent labeling or the like. For enzyme labeling, the enzyme label may be directly bonded to the secondary antibody, or the antibody may be indirectly labeled with the enzyme via a interactive protein pair such as avidin-biotin. Binding of the enzyme to the antibody may also be accomplished, for example, by using a commercially available thiol-introducing reagent to introduce thiol groups into the enzyme and the antibody to be labeled, and then forming S—S bonds between them. The enzyme used may be horseradish peroxidase, alkaline phosphatase, β-D-galactosidase or the like. The enzyme can be detected using a substrate specific for the enzyme. For example, TMB (3,3',5,5'-tetramethylbenzidine) or ABTS (2,2'-azine-di[3-ethylbenzthiazoline sulfonate]) may be used for horseradish peroxidase.

The immunoassay is conducted by mixing the primary antibody-immobilizing carrier, the labeled secondary antibody and the test sample and incubating the mixture, for binding of the SCCA in the test sample onto the primary antibody immobilized on the carrier, and binding of the labeled secondary antibody onto the SCCA molecules.

Thus, the labeled antibody becomes immobilized on the carrier via the SCCA in the sample and the primary antibody immobilized on the carrier, in an amount reflecting the amount of SCCA in the sample. The incubation is carried out in an appropriate buffering solution such as PBS at approximately 4-40° C. and preferably 20-37° C., for a period from 5 minutes to several days, preferably 10 minutes to 24 hours and more preferably 10 minutes to 3 hours.

The unbinding labeled antibody is then separated from the carrier. When the carrier is a solid carrier, the separation procedure can be carried out in a simple manner by solid-liquid separation. When a known amount of labeled secondary antibody is used, it is possible to measure either the carrier-bound labeling or the unbound labeling, or both. When a variable amount of labeled antibody is used, the amount of carrier-bound labeling is detected and measured. Detection of the carrier-bound labeling is preferably accomplished by rinsing the carrier with a rinsing solution such as a buffering solution containing an appropriate surfactant (for example, PBS-Tween20) to remove the unbound labeled antibody. The detection may be carried out by an ordinary method, depending on the type of labeling.

Concrete examples will now be provided for a more detailed explanation of the invention. However, the invention is in no way limited by the examples.

EXAMPLES

1. Elucidation of Relationship Between SCCA and Parakeratosis

Materials and Methods

Materials

Ac-WEHD-MCA, Ac-YVAD-MCA, Ac-VDVAD-MCA, Ac-DEVD-MCA, Ac-VEID-MCA, Ac-IETD-MCA and Ac-LEHD-MCA were purchased from the Peptide Institute, Inc. (Osaka, Japan).

Benzyloxycarbonyl (Z)-YVAD-FMK, Z-YVAD-FMK, Z VDVAD-FMK, Z-DEVD-FMK, Z-VEID-FMK, Z-IETD-FMK, Z-LEHD-FMK, and Z-VAD-FMK were purchased from BioVision (Mountain View, CA). Recombinant caspases 1-10 were obtained from BIOMOL Research Labs, Inc. (Plymouth Meeting, PA).

The proform and large subunit of caspase-14 were detected using H-99 antibody (Santa Cruz Biotechnology, Inc). H-99 antibody is an antibody produced in response to a peptide corresponding to amino acids 24-122 of human caspase-14, and it therefore reacts with caspase-14 proenzyme and its processed form (the large subunit).

The small subunit of caspase-14 was detected using C-20 antibody (Santa Cruz). Cleavage site-specific antibody (h14D$^{146}$) was prepared by immunizing rabbits with the synthetic pentapeptide TVGGD (SEQ ID NO:12) corresponding to the putative processing site of human caspase-14.

Caspase-14 activity was assayed by the method described in Mikolajczyk J. et al., Biochemistry 43, 10560-9 (2004), with some modifications, using Ac-WEHD-MCA as substrate. Briefly, an assay mixture was prepared from 45 μL of 0.1 M HEPES buffering solution (pH 7.5), 0.06 M NaCl, 0.01% CHAPS, 5 mM DTT, 1.3 M sodium citrate and 10 μM WEHD-MCA (all final concentrations). After adding enzyme sample (5 μl) to the mixture, it was incubated for 10-30 minutes. The reaction was suspended by addition of 150 μl of 0.1 M monochloroacetic acid, and Fluoroskan Ascent FL (Thermo Electron Co., Wolsam, Mass.) was used for measurement with a 355 nm excitation wavelength and a 460 nm luminous wavelength. For the inhibitor assay, caspase-14 and peptide inhibitor were incubated at room temperature for 15 minutes in assay buffer, and 5 μl of 100 μM WEHD-MCA was added to start the assay.

Purification of Caspase-14

Human cornified cells (about 14 g) scraped from healthy human heel were extracted with 0.1 M Tris-HCl (pH 8.0) containing 0.14 M NaCl, using a glass homogenizer. After centrifuging at 15,000g for 60 minutes, the supernatant was collected. It was concentrated with Amicon Ultra (Millipore, MA) and desalted with a Fast Desalting Column HR10/10 (Amersham Biosciences), and then the crude product was coated onto a HiPrep 16/10 Q XL column. The column was cleaned with 20 mM Tris-HCl (pH 8.0) and eluted with a 0-1 M linear NaCl gradient. The fraction was tracked by Western blotting using caspase-14antibody (H-99) (Santa Cruz Biotechnology, CA) and h14D$^{146}$ antibody. Each fraction was subjected to assay of hydrolytic activity on Ac Trp-Glu-His-Asp-methyl-coumarinamide (WEND-MCA) (Peptide Institute, Inc., Osaka, Japan). The positive fraction was applied to a Mono Q column equilibrated with the same buffering solution, and eluted with a NaCl gradient of up to 1M. The caspase-14 fraction was further separated by Mono S positive cation exchange chromatography. The column was equilibrated with 20mM acetic acid buffer (pH 4.5) and eluted with a 0-1 M NaCl gradient. The positive fraction was concentrated and applied to a chromatofocusing Mono P column equilibrated with 25 mM ethanolamine (pH 8.3). Next, elution was performed while forming a pH gradient from pH 8 to 5 using 46ml of Polybuffer (pH 5.0). Caspase-14 was subjected to final purification using Superdex 75 gel chromatography. The protein concentration was determined using a BioRad Protein Assay Kit (BioRad Lab, Hercules, CA).

Preparation of Recombinant Caspase-14 and SCCA-1

First, cDNA coding for caspase-14 was isolated and amplified from keratinocyte cDNA by PCR using the forward primer: AAGGATCCAATCCGCGGTCTTTGGAA-GAGGAG (SEQ ID NO: 1) and the reverse primer: TTTCTGCAGGTTGCAGATACAGC-CGTTTCCGGAGGGTGC (SEQ ID NO: 2). The PCR product was cloned in pQE-100 DoubleTag vector (Qiagen, Valencia, Calif.) and expressed in *E. coli* JM109.

The SSCA1 cDNA was separated from a psoriasis cDNA library (Takeda A. et al., J. Invest. Dermatol., 118: 147-54 (2002)) and cloned in pQE30 vector (Qiagen). The recombinant protein was purified with Ni-NTA Agarose (Qiagen) and Mono Q chromatography.

Immunohistochemistry

Human scalp specimens were obtained by plastic surgery with patient consent. The tissue was fixed with 4% paraformaldehyde (PFA) in phosphate buffer (pH 7.4) and embedded in paraffin. Thin sections were prepared and incubated overnight at 4° C. with appropriate antibody. Peroxidase-conjugated goat anti-rabbit IgG (Nichirei Biosciences) was used as the secondary antibody for reaction with DAB as the coloring reagent.

For double immunodetection of TUNEL-positive cells and active caspase, Texas Red™-conjugated anti-rabbit IgG (donkey) was used as the secondary antibody. The TUNEL reaction was carried out using a Fluorescein in situ Cell Death Detection Kit (Roche Diagnostics), according to the manufacturer's instructions.

For Western blotting and immunohistochemical analysis of ICAD, anti-ICAD IgG (FL331, Santa Cruz Biotechnology) and DFF45/ICAD Ab-2 (NeoMarkers, Fremont, Calif.) were used.

Clustered parakeratosis has been frequently reported to be observed in active atopic dermatitis (AD) patient skin (Sakurai K. et al., J. Dermatol. Sci. 30: 37-42 (2002); Piloto Valdes L. et al., Allergol. Immunopathol. (Madr) 18: 321-4 (1990)). In this experiment, localization of ICAD and SCCA-1 in parakeratotic skin was examined using a noninvasive method. The superficial cornified layer was taken from AD or healthy skin, and the medical adhesive Aron Alpha A (Sankyo Co., Tokyo) was used to attach it to slide glass. After fixing with 3% paraformaldehyde, the sample was permeated with 0.1% Triton X-100 and contacted overnight with anti-ICAD or anti-SCCA-1 antibody for immunostaining at 4° C. Alexa Fluor 400-conjugated anti-rabbit (ICAD) or anti-mouse IgG (SCCA-1) were used as secondary antibodies at room temperature for 1 hour. For visualization of the nuclei, the sample was immersed for 5 minutes in a 0.1% pyridium iodide solution and rinsed 3 times with PBS. A Leica DMLA microscope was used for fluorescence observation.

Western Blot Analysis

The protein was separated by SDS-polyacrylamide gel electrophoresis with a 5-20% gradient gel. After electrophoresis, the protein was transferred onto a polyvinylidene difluoride membrane (Immobilon-P, Millipore, Bedford, Mass.) and incubated together with anti-caspase-14 antibody including H-99, h14D$^{146}$ or C20. Peroxidase-labeled anti-rabbit IgG (Sigma) or anti-goat IgG was used as secondary antibody and ECL-Plus (Amersham) was used as immunoreactive protein for visualization by chemiluminescence.

Results

Caspase-14 in keratinocytes is processed at Asp$^{146}$

In Western blot analysis, H-99 antibody was only detected in a 17 KDa band in the keratinocyte extract (FIG. 2). This result does not coincide with the result for extract derived from whole skin or skin-equivalent models that include the unprocessed 30 KDa form. The 17 KDa band is also recognized by h14D$^{146}$ antibody (FIG. 2B), and was therefore conjectured to be the large subunit of active caspase-14 (p17). This suggests that maturation of caspase-14 is accomplished by cleavage at Asp$^{146}$ during the final stage of terminal differentiation. The 30 KDa band is also recognized by H-99 and h14D$^{146}$ antibodies in skin-equivalent models, suggesting cleavage at Asp$^{146}$.

Preparation of Caspase-14 from Keratinocyte Extract

As it is presumed that most of the caspase-14 in keratinocytes is present in the processed form, and therefore in the active form, (Eckhart L. et al., J. Invest. Dermatol. 115: 1148-51 (2000); Lippens S. et al., Cell Death Differ. 7: 1218-24 (2000); Mikolajczyk, J. et al., Biochemistry 43: 10560-9 (2004)), it is believed that human keratinocytes are an excellent source of purified caspase-14. However, it is also known that human keratinocytes contain caspase-1-like enzyme (Takahashi T., J. Invest. Dermatol., 111: 367-72 (1998)). Substrates of caspase-1, such as the WEHD-substrate, can be hydrolyzed by both caspase-1 and caspase-14. The present inventors first tested WEHD-MCA hydrolysis by caspase-1 with 1.3 M sodium citrate and in the presence or absence of 5 mM dithiothreitol. It was confirmed that although WEHD-MCA is an excellent substrate for caspase-1 in. caspase assay buffer, caspase-1 cannot hydrolyze this substrate in the presence of a kosmotropic ion (data not shown). Each fraction was therefore evaluated by three different methods, namely hydrolytic activity for WEHD MCA, reactivity for H-99 and reactivity for h14D$^{146}$ antibody. Table 1 shows the results of continuous chromatography. After the first anion exchange chromatography using a HiPrep Q column, the yield showed a 170% increase and the specific activity increased approximately 10-fold. This increase was probably due to isolation of caspase-14 from endogenous inhibitor. According to Western blotting analysis, fraction Nos. 16-20 contained H-99-positive and 14D$^{146}$-positive bands of molecular weight 17 KDa. These fractions were also found to have WEHD-MCA hydrolytic activity. In subsequent Mono Q anion exchange chromatography, fractions No. 25-No. 29 were found to contain caspase-14 in processed form, based on the presence of 17 KDa H-99-positive and h14D$^{146}$ positive bands. Only these fractions exhibited WEHD-MCA hydrolytic activity. Mono S anion chromatography and Mono P chromatofocusing were effective for removing contaminant protein, and the specific activity increased 3.5-fold and 7-fold, respectively. In this case as well, only the H-99-positive and h14D$^{146}$-positive fractions exhibited WEHD-MCA hydrolytic activity. The final stage with Superdex 75 chromatography separated a 30 KDa molecular weight peak which matched the WEHD-MCA hydrolytic activity peak. SDS-polyacrylamide gel electrophoresis demonstrated that the preparation contained 17 KDa and 11 KDa fragments. The former was positive for both H-99 antibody and h14D$^{146}$ antibody, while the latter was recognized by C20 antibody. This suggested that human caspase-14 was purified as a heterodimer comprising a large subunit (17 KDa) and a small subunit (11 KDa). Also, Superdex 75 gel chromatography demonstrated that, unlike other caspases, caspase-14 in human keratinocytes exists as a monomer similar to the granzyme B-activated form. Table 1 shows a summary of the caspase-14 purification yields. Starting with approximately 100 mg of soluble protein extract there was obtained 11.8 μg of purified protein.

The specific activity increased 764-fold, and the yield was 9.1%.

| Purification of caspase-14 | | | | | | |
|---|---|---|---|---|---|---|
| | Protein concentration μg/ml | Volumes ml | Total protein weight μg | Enzyme activity AFU (mU) | Specific activity (mU/mg protein) | Total activity U | Yield (%) |
| CC TBS Ext | 312.0 | 320.00 | 99840.0 | 3.67 | 11.8 | 587.34 | 100.0 |
| Hi Prep Q | 1185.0 | 15.00 | 17775.0 | 133.59 | 112.7 | 1001.92 | 170.6 |
| Mono Q | 582.0 | 8.00 | 4656.0 | 150.30 | 258.2 | 601.19 | 102.4 |
| Mono S | 61.3 | 8.00 | 490.4 | 56.94 | 928.8 | 227.75 | 38.8 |
| Mono P | 50.5 | 1.00 | 50.5 | 338.31 | 6699.2 | 169.15 | 28.8 |
| Superdex 75 | 11.8 | 1.00 | 11.8 | 106.52 | 9015.1 | 53.26 | 9.1 |

Enzyme Properties of Purified Caspase-14

The enzyme properties of the purified caspase-14 were examined (FIGS. 3 and 4). The caspase-14 exhibited sensitivity to a variety of caspase inhibitors including YVAD-FMK (SEQ ID NO:3) (caspase-1 inhibitor), VDVAD-FMK SEQ ID NO:4) (caspase -2 inhibitor), DEVD-FMK (SEC) ID NO:5) (caspase-3 inhibiror, IETD-FMK (SEQ ID NO:7) (caspase-8 inhibitor), LEHD-FMK(SEO ID NO:8) (caspase-9 inhibitor) and VAD-FMK (pan-caspase inhibitor) (FIG. 3). VEID-FMK (SEQ ID NO:6) had virtually no effect. YVAD-FMK (SEQ ID NO:3) exhibited the most powerful inhibiting effect against caspase-14 activity. This is probably due to structural similarity between caspase-1 and caspase-14. The pan-caspase inhibitor VAD-FMK inhibited caspase-14 activity at about the same level as VAD-FMK. The class-specific inhibitor iodoacetic acid (IAA) for cysteine proteinases or the class-specific inhibitor 4-(2-aminoethyl)benzenesulfonyl fluoride (AEBSF) for serine proteinases exhibited no significant inhibiting effect at the test concentrations in this experiment.

Effect of Purified Caspase-14 on ICAD Decomposition

The present inventors tested the effect of caspase-14 on ICAD, in the course of searching for natural substrates of caspase-14, because disappearance of nuclei is a very important event for final differentiation. When purified caspase-14 was incubated together with recombinant ICAD protein in ordinary caspase assay buffer, analysis by Western blotting using anti-ICAD IgG showed absolutely no hydrolytic activity of the purified caspase-14 for ICAD (FIG. 4A). In the presence of a kosmotropic salt, however, intact ICAD protein was reduced and the two major decomposition products were increased, thus indicating that purified caspase-14 has a limited decomposing effect on ICAD.

Caspase-14 is Inhibited by SCCA-1

Although SCCA-1 belongs to the serpin superfamily, it inhibits cysteine proteinases such as papain and cathepsin L (Takeda A. et al., Biol. Chem. 383, 1231-6 (2002)). This indicates that SCCA-1 is an inherent crossclass inhibitor similar to Crm-A$^{32}$ The present inventors therefore tested whether or not SCCA-1 can inhibit caspase members. Kosmotropic conditions were used for caspase-14. When recombinant active caspases were incubated together with SCCA-1, none of the caspase members (1-10) were affected in their enzyme activity. However, SCCA-1 inhibited caspase-14 activity against WEHD-MCA in a dose-dependent manner (FIG. 4C). SCCA 1 also inhibited ICAD decomposition by caspase-14. The enzyme activity was not recovered even with extended incubation. This suggests strong binding between caspase-14 and SCCA-1 (FIG. 4B).

Localization of Active Caspase-14 and TUNEL-Positive Cells

Figure 5:
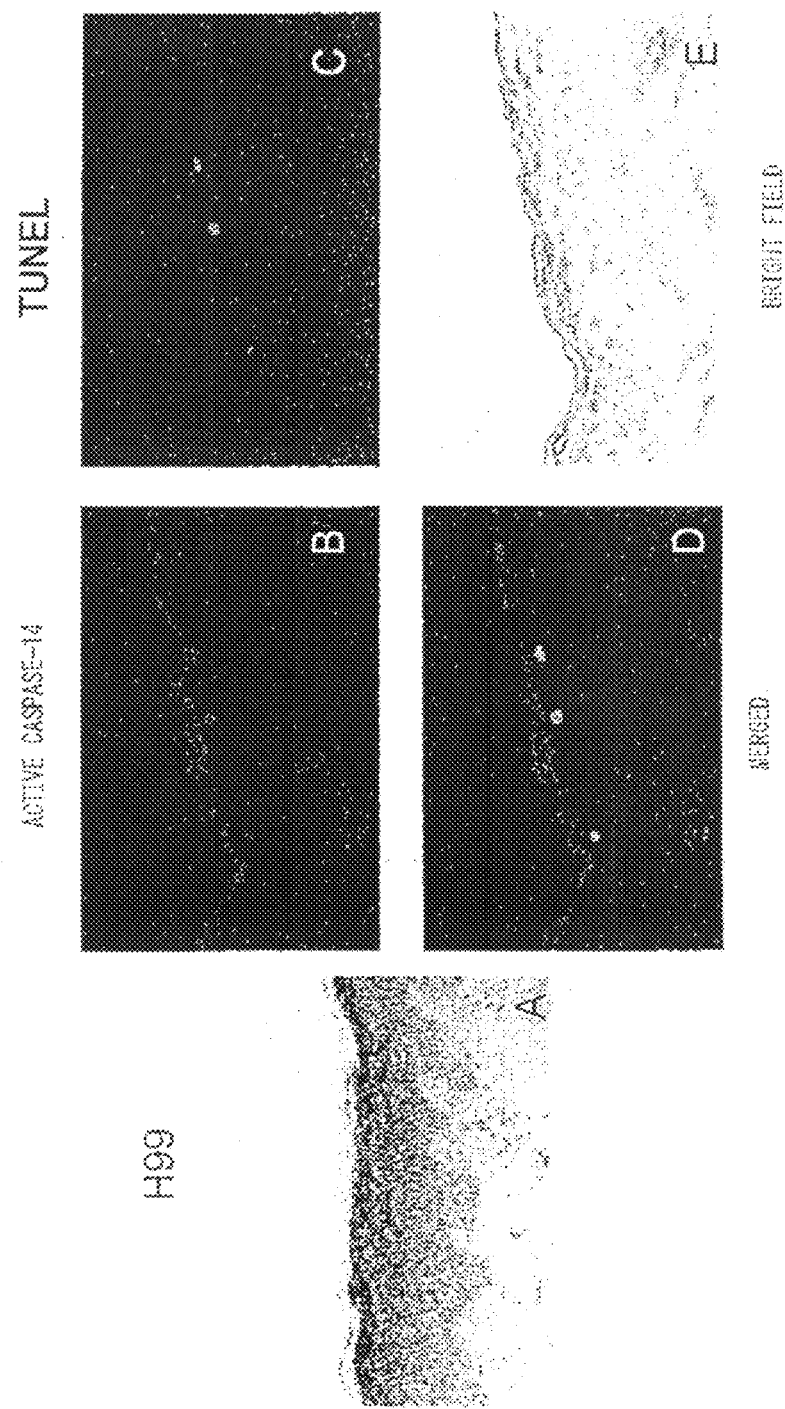
FIG. 5 shows localization of active caspase-14 and TUNEL positive cells. Thin sections of normal human skin were stained with H-99 antibody (A), h14D$^{146}$ antibody (B) or TUNEL (C). Texas-Red was used for fluorescence detection (B). FITC was used for TUNEL, Texas Red was used for immunostaining and double staining was carried out for TUNEL and caspase. (D) shows a superimposed image, and (E) shows the bright field.

In order to determine whether or not caspase-14 is involved in the denucleation process, the present inventors performed double staining of active caspase-14 and TUNEL. As shown in FIG. 5A, caspase-14 including the proform and active form was localized from squamous cells to cornified cells in normal human epidermis. This is in concurrence with past findings (Lippen S. et al., (2000), ibid). Active caspase-14 detected with h14D$^{146}$ antibody was limited to some cornified cells and granulocytes (FIG. 5B). Most of the cornified cells were ubiquitously stained. TUNEL-positive cells were observed just below the cornified layer, but most of these positive cells were highly confined (FIG. 5C). Interestingly, the TUNEL-positive cells were completely localized together with h14 D$^{146}$-positive cells. This suggests that DNA fragmentation had occurred in the cells, and that active caspase-14 is involved in the process.

Co-Localization of ICAD and SCCA-1 in Parakeratotic Nuclei

In normal human epithelium cross-sections, using FL331 antibody demonstrates that most localization of ICAD is in the nuclei of basal cells and suprabasal cells. The cytoplasms were weakly positive from basal cells to granular cells. Immunoreactivity for ICAD in the cornified layer was drastically reduced.

Figure 6:
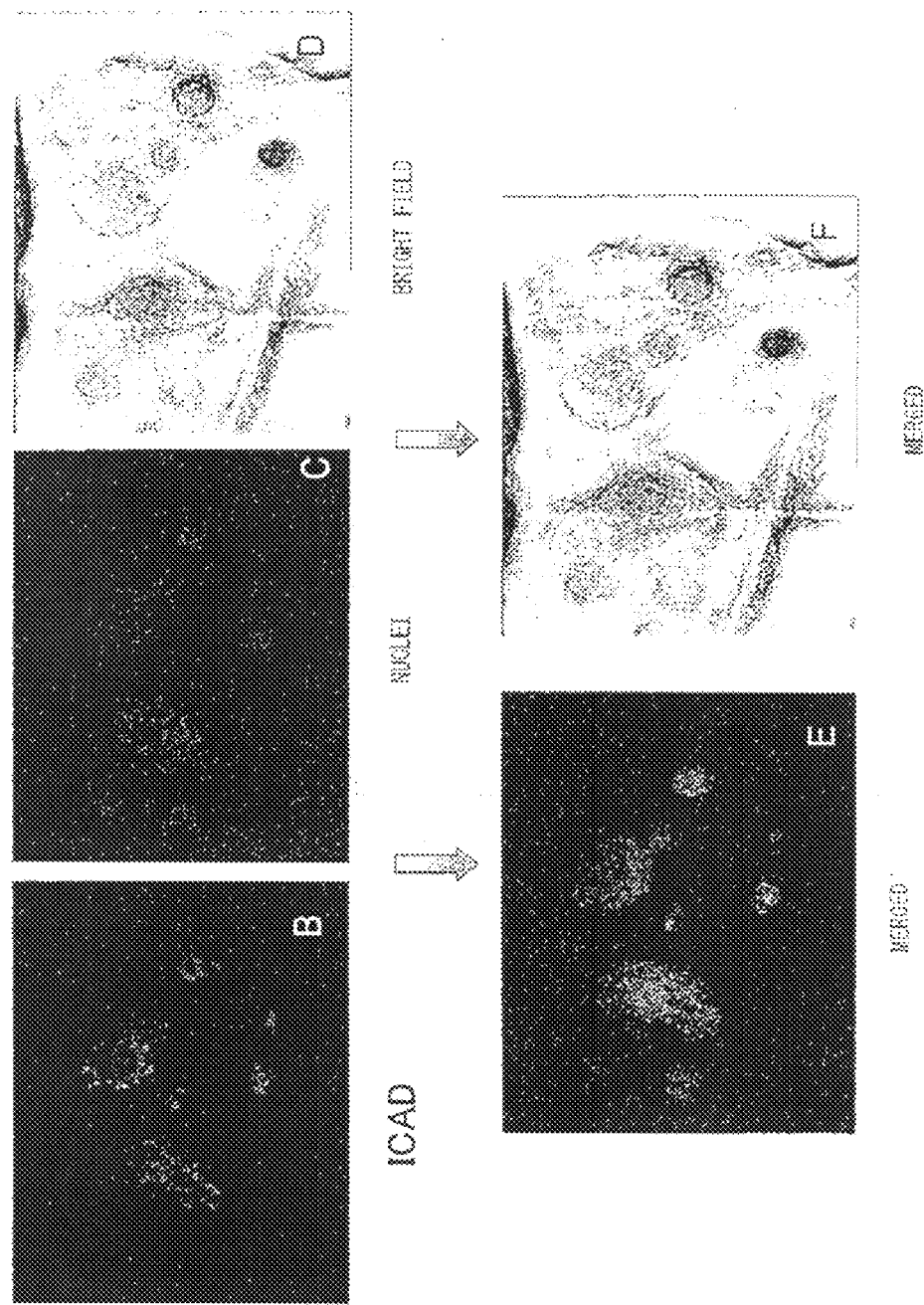
FIG. 6 shows co-localization of ICAD and parakeratotic nuclei in the skin surface. Thin sections of normal human skin were stained with anti-ICAD antibody FL331. Almost all of the nuclei of the lower epidermis were positive for the antibody. ICAD on the superficial layer of keratinocytes from AD patient skin was stained with this antibody, and positive sites with different sizes were observed (B). Nuclear staining with propidium iodide (PI) was noted frequently, indicating nuclear clusters (C). Bright field observation of the same sites indicated overlapped scales on the surface (D). The superimposed image revealed the presence of ICAD only at sites of parakeratosis (E). Superimposed images of nuclear stain in the bright field were also seen (F).

Substantially the same results were found even when using the N-terminal peptide specific-antibody DFF45/ICAD Ab-2 (data not shown). When AD patient superficial cornified layer was stained with anti-ICAD antibody (FL-331), cluster regions of various sizes were positive for the antibody (FIG. 6B). Nuclear staining with PI indicated that parakeratotic nuclei were always present in the island-like patches (FIG. 6C). The bright field of the superficial cornified layer showed a highly irregular rough surface (FIG. 6D). The superimposed image showed is matching between the parakeratotic sites and ICAD-positive sites (FIGS. 6E and 5F). These results suggest that ICAD decomposition is necessary for elimination of nuclei in terminal differentiation.

Figure 7:
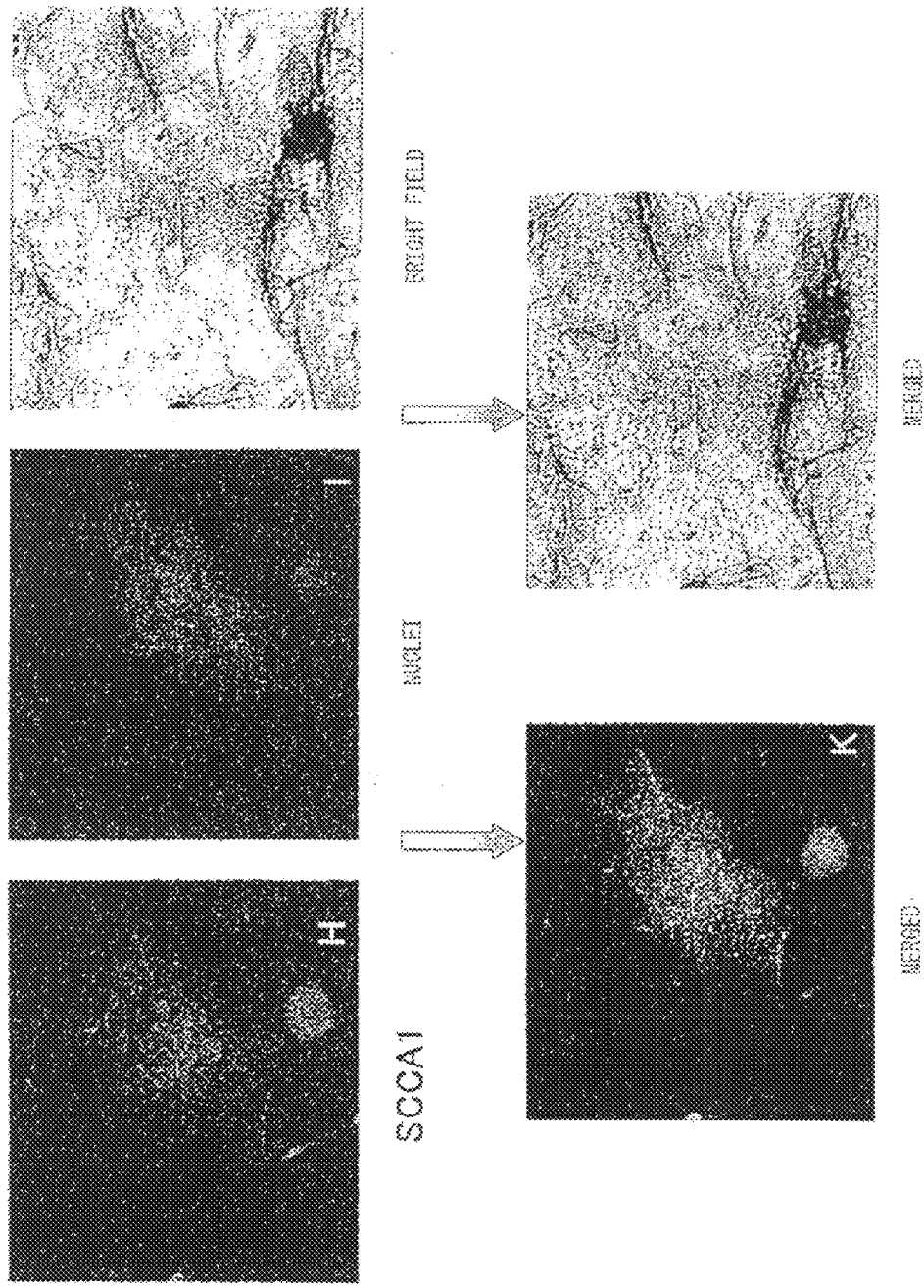
FIG. 7 shows co-localization SCCA-1 and parakeratotic nuclei, SCCA-1 was virtually undetected in normal skin surface. SCCA-1-positive sites were seen in the superficial layer of AD patient skin (H). Nuclear clusters were found only at these sites (I) — The bright field is shown in (J). The superimposed image indicates overlapping of SCCA-1-positive sites, preferably with sites containing undigested nuclei (K). Separate superimposed images corresponding to SCCA-1 staining and the bright field are shown (L).

In the case of normal skin, a very low level of SCCA-1 is detected in the granular layer. Immunostaining with significantly high patchy distribution of positive sites was also observed in superficial cornified layer with active AD (FIG. 7H). Similarly, the SCCA-1-positive regions matched the PI-positive nucleus layer, i.e. the parakeratotic sites (FIG. 7J-L). To summarize the results, the ICAD/CAD system plays a major role in the denucleation process, and SCCA-1 acts as a suppressor in the reaction.

Discussion

Caspase-14 is expressed primarily in the epidermis and is virtually unexpressed in other tissues (Van de Craen M. et al., Cell Death Differ. 5, 836-46 (1998)). Past reports have shown a link between terminal differentiation of keratinocytes and processing of caspase-14, and this has suggested acceleration of the protease activity of caspases (Lippen S. et al., Cell Death Differ 7, 1218-24 (2000); Eckhart L. et al. Biochem. Biophys. Res. Commun. 277: 655-9 (2000); Hu S. J. Biol. Chem 273: 29648-53 (1988)). Recently, Mikolajaczyk et al., (2004) (ibid) demonstrated that granzyme B-cleaved caspase-14 is enzymatically active in the presence of kosmotropic salts. In this research, the present inventors attempted to purify caspase-14 from fully differentiated keratinocytes in order to examine whether or not human caspase-14 is active in the final stage of keratinocyte differentiation. The present inventors used three different antibodies recognizing the large subunit, the pro form (H-99) (having a putative caspase cleavage site at $Asp'^{146}$ ($h14D^{146}$)) and the small subunit (C20). The final preparation consisted of two protein bands, specifically a 17 KDa protein band recognized by $h14D^{146}$ antibody and a 11 KDa protein band recognized by C20 antibody. These protein bands are large and small subunits of active caspase-14. The H-99-positive 17 KDa band was recognized together with $h14D^{146}$ antibody during the purification step. This suggests that the large subunit ends with $Asp^{146}$ at the carboxyl terminus. The amino-terminal region of the small subunit was identified as $Lys^{153}$-Asp-Ser-Pro-Gln (SEQ ID NO:11), suggesting that processing occurred between $Ile^{152}$ and $Lys^{153}$. This site is an unusual cleavage site for a caspase member. This site is an unusual cleavage site fora caspase member. This is also in harmony with the findings of Chien A.J. et al. (Biochem. Biophys. Res. Commun. 296(4): 911-7 (2002 Aug. 30)) that caspase-14 immunoprecipitated from prepuce extract is cleaved at the same site. It was therefore concluded that human caspase-14had been homogeneously purified as a highly active heterodimer. It was also suggested that processing at the two sites $Asp^{146}$ and $Ile^{152}$ and removal of the six residues in the linker region between $Xxx^{147}$ and $Ile^{152}$ are involved in caspase-14maturation. The existence of two different cleavage sites (one acidic and the other hydrophobic) also suggests that activation of caspase-14takes place in a multistage manner by multiple enzymes.

The enzymatic properties of purified caspase-14 were highly unique. Purified caspase-14exhibited relatively wide inhibitor sensitivity with respect to known caspase inhibitors. In particular, the caspase-1 inhibitor YVAD-FMK exhibited the strongest inhibition. YVAD-FMK exhibited higher activity than WEHD-MCA and another caspase-1 substrate YVAD-MCA. This suggests a close relationship between caspase-1 and caspase-14. However, the present inventors have shown that caspase-14 has significantly different properties. It was shown, for the first time, that SCCA-1 is an endogenous inhibitor of caspase-14. The property most specific to SCCA-1 is its high specificity for caspase-14. The other members, caspases 1-10, had never been reported as being affected by SCCA-1. SCCA-1 did not inhibit caspase-3activity when using the synthetic substrate DEVD-MCA or the natural substrate ICAD. This behavior is in contrast to Crm A. Can A is also known to suppress several caspases including caspase-1 and caspase-8 (Gagliardini V. et al., Science 263: 826-8 (1994)). XIAP is known to inhibit caspase-3, -7, and -9 (Srinivasula S.M. et al., Nature 410: 112-6 (2001)). Since the anti-apoptotic protein p35 inhibits caspase-1, -3, -6, -7, -8, and -10, it is believed to have a wider spectrum. The fact that all of these inhibitory proteins Crm A, IAP and p53 can suppress some initial and active caspases suggests that these molecules participate in activation of the classic apoptotic pathway. On the other hand, the results by the present inventors strongly suggest that SCCA-1 is not a key player in ordinary apoptosis but is an important regulator in the denucleation process mediated by caspase-14.

The molecular mechanism for this process had not yet been elucidated. The present inventors have demonstrated that human caspase-14 can decompose ICAD in the presence of a kosmotropic salt. ICAD (also known as the DNA fragmenting factor "DFF45") is an inhibitor for magnesium-dependent endonucleases known as caspase-activated DNases (CAD) (or DFF40). The ICAD/CAD system plays an important role in decomposition of chromosomal DNA during apoptotic cell death. ICAD bound to CAD exists as an inactive complex. Caspase-3 exhibits limited proteolysis of ICAD, cleaving it at the two sites $Asp^{117}$ and $Asp^{224}$. The cleavage activates CAD to initiate DNA degradation (Nagata S. Exp. Cell Res. 256, 12-8 (2000)). Caspase-3 is not necessarily required for cleavage of most of the cellular protein during apoptosis, but it is necessary for cleavage of ICAD (Tang D. et al., J. Biol. Chem. 273, 28549-52 (1998)). This means that caspase-3 is very important for DNA fragmentation while other active caspases, namely caspase-6 and 7, are not important. Interestingly, caspase-14 produced similar 12 KDa and 35 KDa cleavage fragments from ICAD. Sequence analysis revealed the same cleavage site. This suggests that caspase-14 can serve as a total substitute for caspase-3. Although caspase-14 can decompose ICAD, it is clearly different from the pro-apoptosis caspase-3 for the following reasons. First, overexpression of caspase-14 does not induce apoptotic cell death (Van de Craen. Cell Death Differ. 5, 838-46 (1998)). This is in contrast to caspase-3. Secondly, caspase-14 is not activated by various apoptotic stimuli (Lippens et al. (2000), ibid). Initial caspase or other caspase members were not able to process pro-caspase-14, and this is in agreement with past observations (Lippens et al. (2000), ibid). Activation only occurs during terminal differentiation (Eckhart L. et al., (2000), ibid). Thirdly, caspase-14 synthesis is limited to differentiating keratinocytes in adult tissue (Eckhart L. Biochem. Biophys. Res. Commun. 277, 655-9 (2000)). The ability of caspase-14 to cleave ICAD is regulated in quite a different manner than caspase-3. ICAD degradation by caspase-14 requires an abnormally high concentration of kosmotropic ions. Other caspases are virtually inactive at such an ion concentration. From a general viewpoint, since activation of caspase-14 is regulated by the keratinocyte differentiation program, it is believed to have a special role among the caspase members.

Further support for the function of the ICAD/CAD system in terminal differentiation of keratinocytes is provided by in vivo experiments. Immunohistochemical research has shown that ICAD is present in the nuclei of basal keratinocytes and squamous keratinocytes, disappearing in granular cells, and that disappearance of nuclei occurs during terminal differentiation. Positive immunostaining of ICAD was seen in the patchy sites of AD patient superficial epidermis. These regions have slightly rough surfaces and low semi-transparency. PI-positive, undigested nuclei aggregates were in fact co-localized in these regions, whereas other regions were not dyed by anti-ICAD antibody. The tape stripping sample from AD patient skin showed the presence of intact ICAD protein, but no detection was found in healthy extracts. These results suggest that ICAD is involved in the denucleation process during terminal differentiation.

Virtually no SCCA-1 is expressed in normal epidermis. On the other hand, expression has been reported to be high in psoriatic epidermis, the oral mucosa and the esophagus (Takeda A. et al., J. Invest. Dermatol. 118, 147-54 (2002)). Interestingly, parakeratosis is also present in such tissue. The present inventors have demonstrated that strong SCCA-1 staining is also found in parakeratotic sites. SCCA-1 and ICAD were consistently co-localized at the same sites where nuclei aggregates were found. Since there were no other epidermal surface areas negative for SCCA-1 or ICAD, the co-localization of these molecules at the parakeratotic sites suggests that the molecules are involved in suppressing the denucleation process. It has been reported that the pan-caspase inhibitor VAD-FMK inhibited disappearance of nuclei in skin equivalent models (Weil et al., 1999). The discovery of the present inventors that VAD-FMK is one of the most powerful caspase-14 inhibitors increases the possibility that caspase-14 is a candidate in this reaction. Caspase-14 is downregulated in parakeratotic sites of psoriatic skin, and is not found in oral epidermis. In the oral epidermis, disappearance of nuclei is either impaired in some manner, or does not occur (Lippens et al., (2000), ibid). Interestingly, SCCA-1 is upregulated in these tissues. It is thought likely that abnormal expression of these molecules leads to incomplete differentiation, including the permanent presence of nuclei.

The activation mechanism of caspase-14 in the skin is not fully understood. Activation is only observed in skin or skin-equivalent models, and not in cell culture systems (Eckhart L. et al. (2000), ibid). The present inventors conducted actual testing under different conditions. The conditions included addition of serum, extending the culturing period to the 14th day after confluence in the presence or in the absence of calcium, treatment with the calcium ionophore A23187, or exposure to air for a 30 minute period sufficient to upregulate most differentiation markers. Although these differentiation stimuli induce caspase-14 mRNA expression, none were effective to produce caspase-14 activation (data not shown). The activation process is strictly controlled and is strongly inhibited in monolayer cultures. It is believed that stratification and air exposure are necessary for activation. Clearly, activation of caspase-14 does not depend on the apoptosis program but is controlled by the differentiation program. During the terminal differentiation process, many proteinases are activated, including serine, cysteine and aspartic acid proteinases. Trypsin-like and chymotrypsin-like serum proteinases presumably play a role in denucleation of the outermost keratinocytes. Some cysteine proteinases, such as cathepsin B and L, are upregulated in differentiated keratinocytes. Cathepsin D and aspartic acid proteinases are also putatively involved in denucleation of keratinocytes. These enzymes also sometimes contribute to other differentiation mechanisms such as activation of caspase-14, for example.

To summarize the above, the present inventors purified caspase-14 from human keratinocyte extract. Caspase-14 induces disappearance of nuclei seemingly by apoptosis, but it is strongly suggested that the changes are distinguishable changes via ICAD degradation in the final stage of keratinocyte differentiation. While the process involves several apoptotic factors, it is not a cell death process leading to the elimination of damaged cells but rather is a constitutive process completing an overall structure that performs a barrier function as its major role. Abnormal expression of caspase-14 or SCCA-1 directly affects the differentiation program, resulting in parakeratosis and loss of the barrier function.

2. Evaluation of Skin Condition as an Indicator of SCCA Expression by Skin Stratum Corneum Cells Materials and Methods (1) Antibodies Polyclonal antibodies recognizing both SCCA-1 and 2 were prepared using SCCA (SCCA-1 and SCCA-2) purified from psoriatic epidermis scales. After centrifuging psoriatic epidermis scale extract (extract: 0.1 M Tris-HCl (pH 8.0), 0.14 M NaCl), the supernatant was purified with Sephacryl S-200, DEAE Sepharose, Mono Q, Mono S, Mono P, Superose 6 and using as antigen for immunization of rabbits.

Anti-SCCA-1 monoclonal antibody and anti-SCCA-2 monoclonal antibody were obtained from Santa Cruz Biotechnology, CA, USA.

(2) Immunohistochemical Examination

Epidermis specimens were fixed with cold acetone and then embedded in paraffin, according to the AMeX protocol (Sato Y. et al. Am. J. Pathol., 125, 431-435 (1986)). Sections were deparaffinized with xylene and rinsed with acetone and then PBS. The nonspecific binding sites of the sections were blocked with 10% normal goat serum (Histofine, Tokyo, Japan).

The epidermis sections were incubated with anti-SCCA-1 monoclonal antibody (1:500 dilution), anti-SCCA-2 monoclonal antibody (1:500 dilution) purified as described above or anti-SCCA polyclonal antibody (1:500 dilution). After rinsing with PBS, the sections were colored with a DAKO Envision System (DAKO Corp., CA, USA) and then counterstained with haematoxylin and observed.

(3) ELISA

Skin stratum corneum samples were taken by tape stripping, wherein transparent adhesive tape (Cellotape™ by NICHIBAN) was attached to the skin surface and then peeled off. After attachment to the skin stratum corneum, the tape was cut, immersed in extraction buffer (0.1 M Tris-HCl (pH 8.0), 0.14 M NaCl, 0.1% Tween-20, 1 ml), and subjected to ultrasonic treatment (20 sec×4) to prepare a sample extract.

Polyclonal SCCA antibody diluted with PBS (1:1000 dilution) was dispensed at 100 μl into each well of a 96-well ELISA plate and allowed to stand overnight at room temperature for binding to the solid phase of the plate. In order to inhibit nonspecific binding to the plate, incubation was performed for 1 hour with a blocking solution (solution of Blockace diluted with PBS-Tween 20, 300 μl/well).

To each well of the ELISA plate there was added 50 μl of sample extract, and reaction was conducted at 37° C. for 2 hours. Monoclonal SCCA-1 antibody (1:1000 dilution) or monoclonal SCCA-2 antibody (1:1000 dilution) was added and reaction was continued at 37° C. for 1 hour. Next, horseradish peroxidase-labeled anti-mouse secondary antibody was added for reaction at 37° C. for 1 hour, and after rinsing with 0.1% Tween-20 PBS, 3',3',5', tetramethylbenzidine (TMB) substrate was added, a TMB Peroxidase EIA substrate kit (BIO-RAD) was used for coloring, and measurement was performed at 630 nm.

(4) Measurement of Transepidermal Water Loss (TEWL)

The TEWL measurement of the specimens (healthy human face and inner arm) was carried out using a TEWAmeter (TM120).

Results
(1) Immunohistochemical Examination

Figure 8:
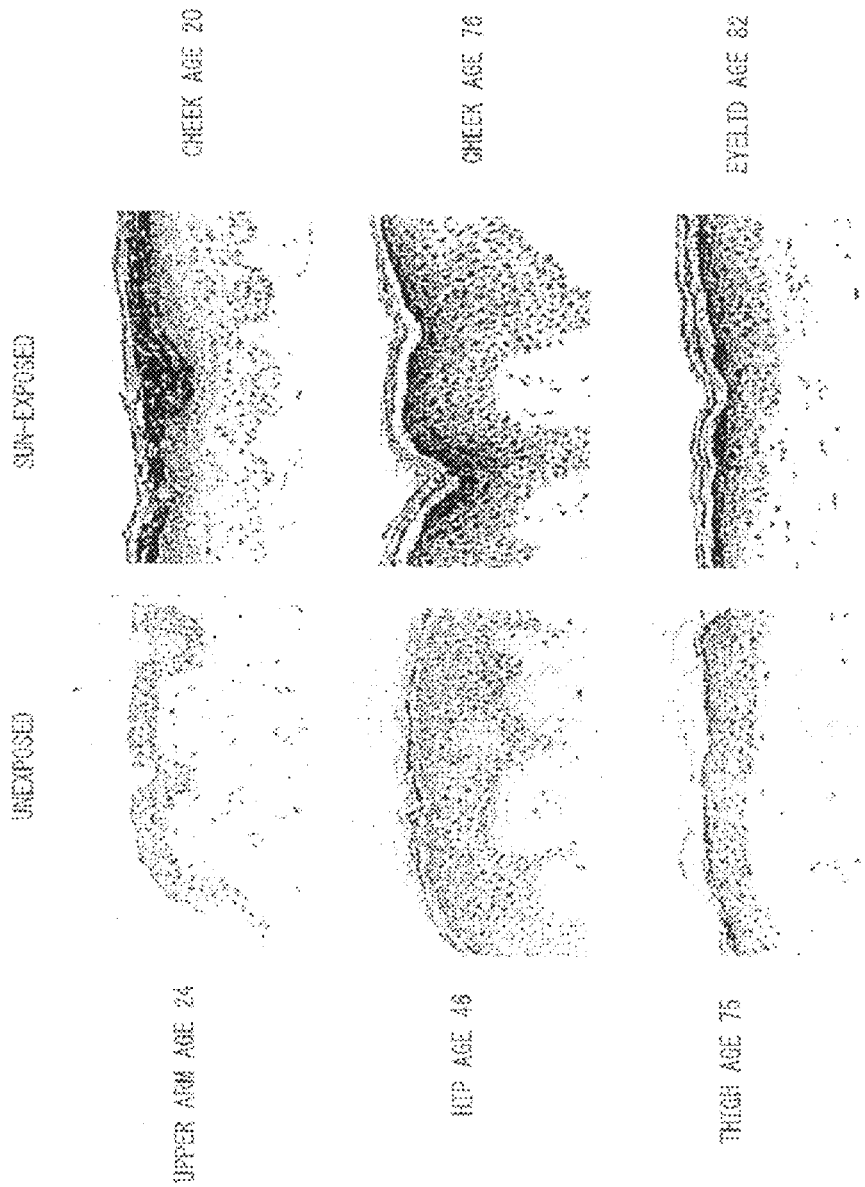
FIG. 8 shows the results of immunohistochemical examination, indicating SCCA expression in the epidermis at exposed and unexposed areas.

FIG. 8 shows results from microscope observation of epidermis specimens from the upper arm (human, age 24), hip (human, age 46) and thigh (human, age 75) as unexposed areas (areas that are unexposed to sunlight relatively infrequently), and epidermis specimens from the cheek (human, ages 20, 76) and eyelid (human, age 82) as exposed areas (areas that are exposed to sunlight relatively frequently), using as the antibody anti-SCCA polyclonal antibody that binds both SCCA-1 and SCCA-2. From FIG. 8 it is seen that SCCA was significantly increased in the upper epidermis at exposed areas that are constantly exposed to more harsh conditions such as ultraviolet rays, compared to unexposed areas.

Figure 9:
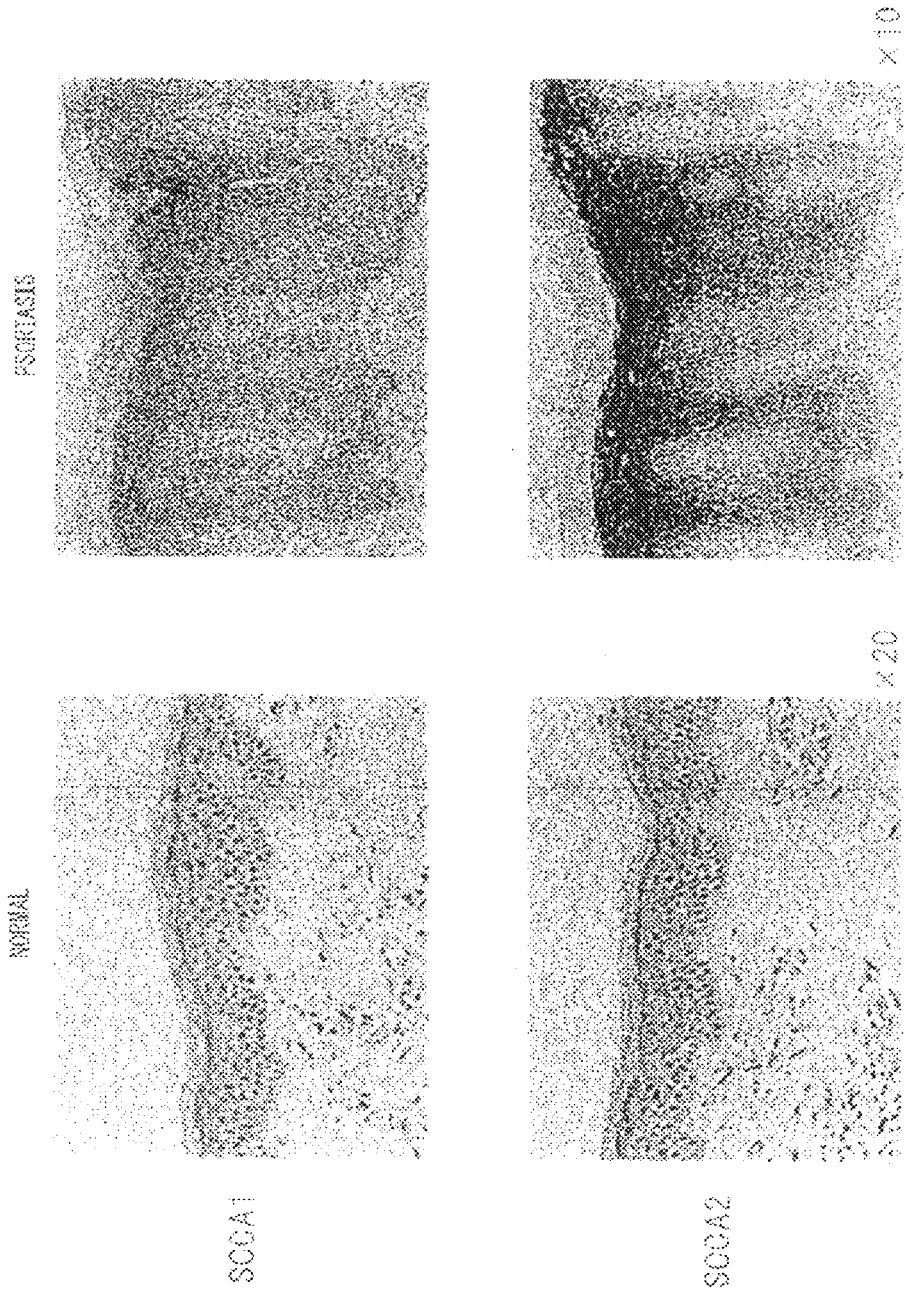
FIG. 9 shows the results of immunohistochemical examination showing SCCA expression in normal skin and psoriatic skin.

FIG. 9 shows expression of SCCA-1 and 2 in normal upper epidermis (50-year-old male) and psoriatic upper epidermis. As these photographs clearly show, SCCA-1 and 2 were only weakly expressed in normal skin, whereas both SCCA-1 and 2 were more notably expressed in psoriatic skin, an inflammatory parakeratotic condition.

It was concluded as a result that SCCA expression is significantly promoted in exposed and parakeratotic areas of skin, compared to the stratum corneum of healthy skin.

(2) ELISA

1) SCCA Expression in Normal Skin Stratum Corneum

Figure 10:
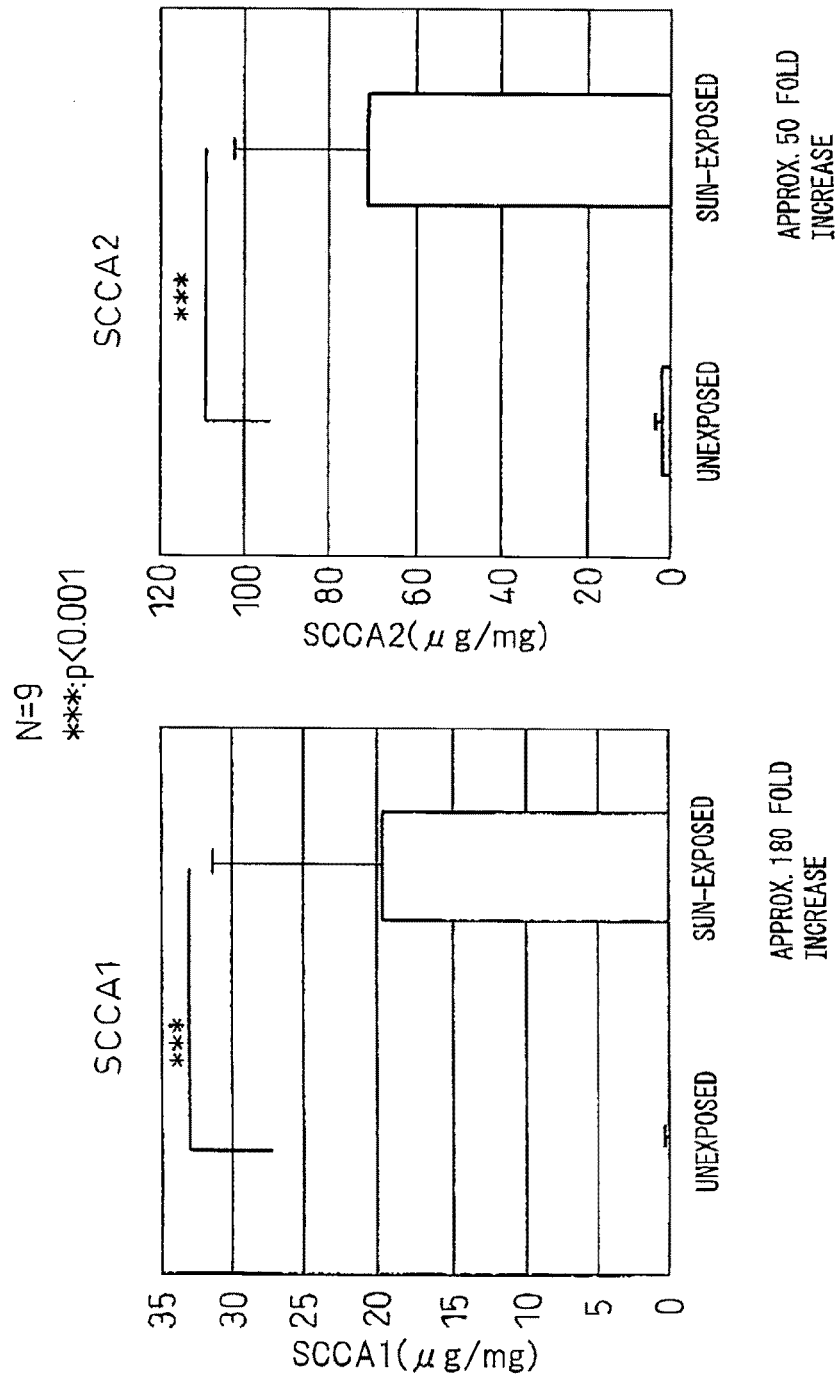
FIG. 10 shows the results of SCCA measurement in normal skin stratum corneum by ELISA.

Stratum corneum was taken from exposed areas of skin exhibiting a healthy skin condition (face and cheek) and unexposed areas of skin exhibiting a healthy skin condition (inner arm) by tape stripping, and the SCCA-1 and SCCA-2 expression levels were measured by ELISA. The results are shown in FIG. 10.

Expression of SCCA-1 and 2 was notably accelerated in exposed areas compared to unexposed areas. Thus, ELISA allows quantitative determination that SCCA, and particularly SCCA-1 is significantly promoted in the upper epidermis at exposed areas that are constantly exposed to harsh environments, even if they exhibit healthy properties, compared to unexposed areas.

2) SCCA Expression in Psoriatic Skin Stratum Corneum

Figure 11:
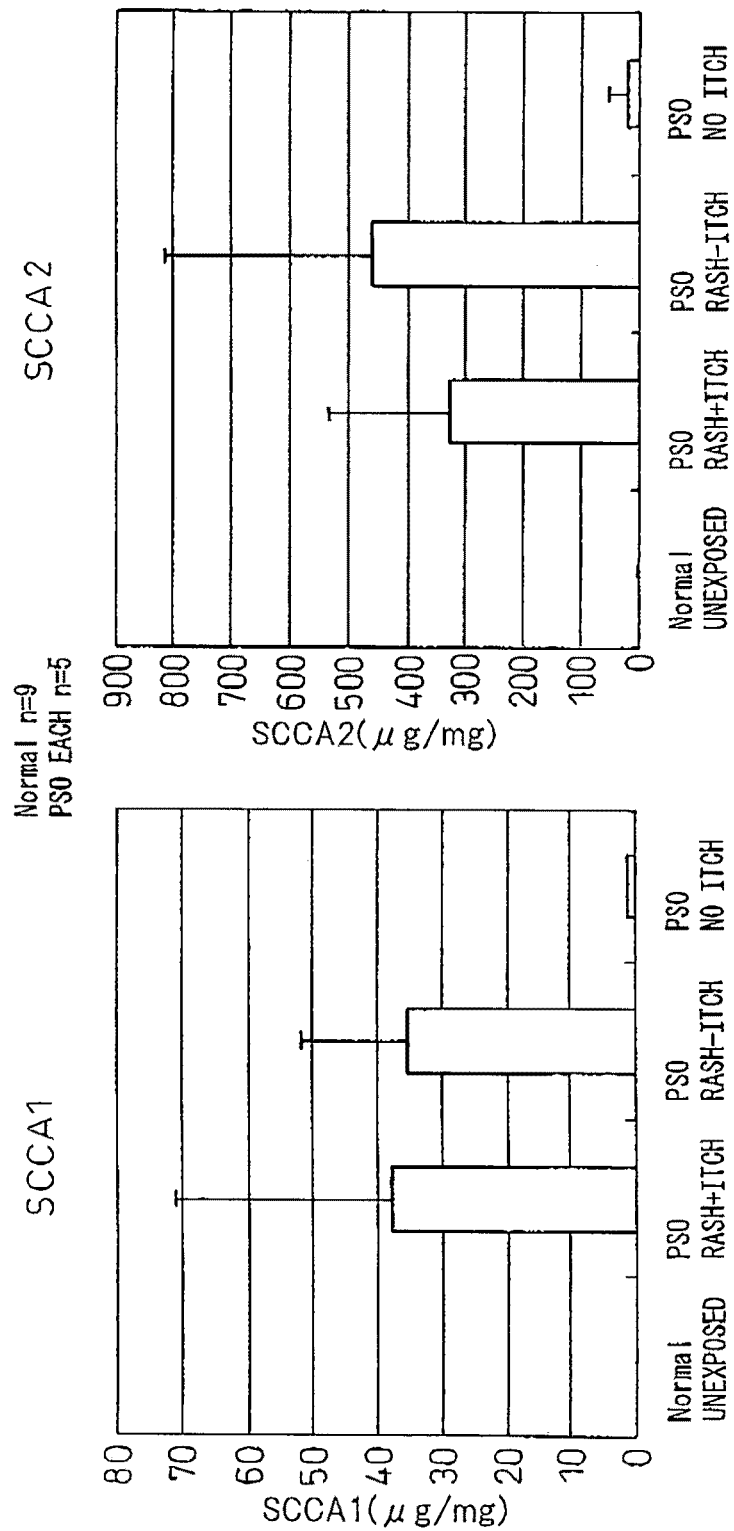
FIG. 11 shows comparative results for SCCA measurement in normal skin and psoriatic skin stratum corneum by ELISA.

Tape stripping from the skin of individuals exhibiting a healthy skin condition (unexposed area: inner arm) and the skin of patients suffering from psoriasis was carried out to obtain stratum corneum, and the SCCA-1 and SCCA-2 expression levels were measured by ELISA. As psoriasis patient skin areas, there were tested rash areas with itching, rash areas without itching, and non-rash areas. The results are shown in FIG. 11.

While virtually no expression of SCCA-1 or -2 is observed in skin stratum corneum of healthy individuals, significantly increased expression of SCCA-1 and -2 was found in the stratum corneum of rash areas of psoriasis patients regardless of whether or not it was accompanied by itching. Incidentally, almost no expression of SCCA-1 or -2 was found even in psoriasis patients in skin areas with no psoriasis symptoms (non-rash areas).

3) SCCA Expression in Atopic Dermatitis Skin Stratum Corneum

Figure 12:
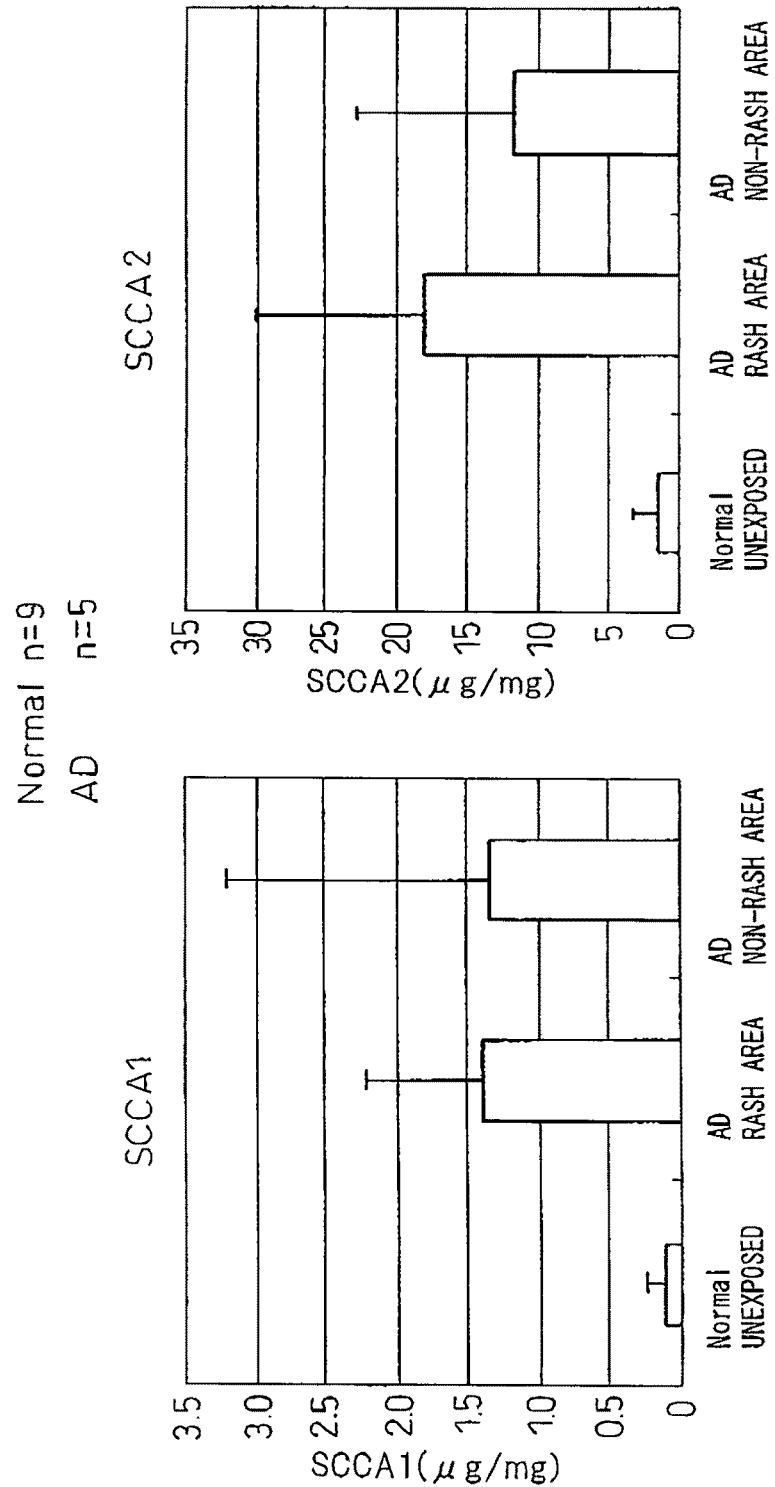
FIG. 12 shows comparative results for SCCA measurement in normal skin and atopic dermatitis skin stratum corneum by ELISA.
Figure 13:
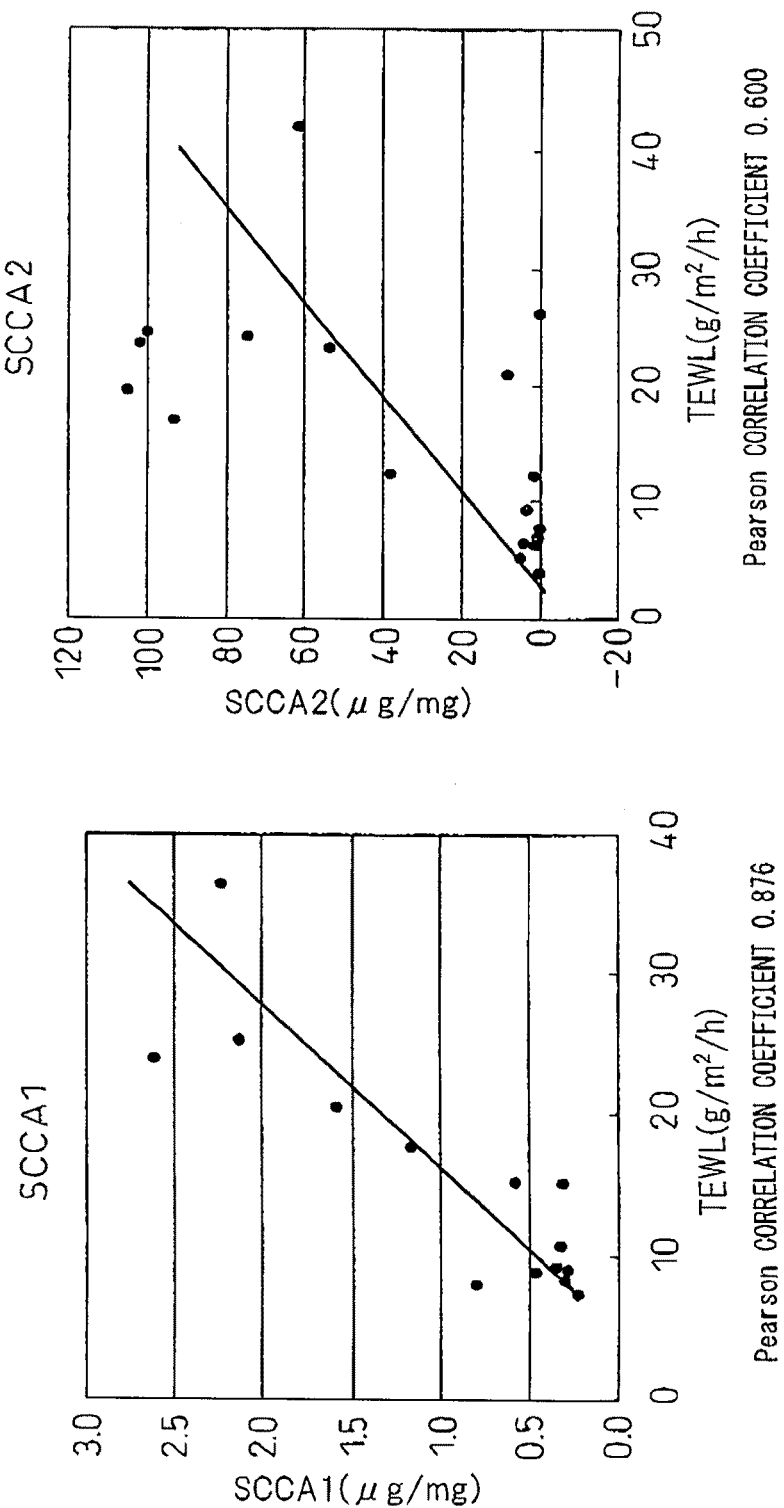
FIG. 13 shows the correlation between SCCA amount and TEWL in normal skin.

Tape stripping from the skin of individuals exhibiting a healthy skin condition (unexposed area: inner arm) and the skin of patients suffering from atopic dermatitis was carried out to obtain stratum corneum, and the SCCA-1 and SCCA-2 expression levels were measured by ELISA. Rash areas and non-rash areas were tested as atopic dermatitis patient skin areas. The results are shown in FIG. 12.

While virtually no expression of SCCA-1 or -2 is observed in skin stratum corneum of healthy individuals, significantly increased expression of SCCA-1 and -2 was found in the stratum corneum of affected areas of atopic dermatitis patients, whether they were rash areas or non-rash areas. In the case of atopic dermatitis, therefore, it is possible to diagnosis the condition using SCCA-1 and/or -2 as a marker even before symptoms of atopic dermatitis appear. Thus, SCCA can be used as a marker to judge susceptibility to atopic dermatitis, thus allowing prevention and early treatment (for example, before onset).

4) Correlation Between SCCA Expression and Transepidermal Water Loss (TEWL)

SCCA expression in skin stratum corneum was measured by ELISA and TEWL was also examined as a skin physiological parameter, to determine the correlation between SCCA expression and TEWL. The results are shown in FIG. 12. For SCCA-1 and TEWL the Pearson correlation coefficient was 0.876 while for SCCA-2 and TEWL the Pearson correlation coefficient was 0.600, both of which were significant correlations, and therefore it was demonstrated that high TEWL with relatively poor skin condition is accompanied by increased expression of SCCA-1 and -2, and especially SCCA-1.

5) SCCA Expression in Pollen Hypersensitive Skin Stratum Corneum

Skin from an individual exhibiting a healthy skin condition (control) and skin from a patient suffering from roughened skin due to pollen hypersensitivity were sampled by tape stripping to obtain the stratum corneum, and the correlation between pollen hypersensitive roughened skin and TEWL was examined while also measuring SCCA-1 expression in the pollen hypersensitive roughened skin by ELISA. The skin areas selected were the inner arm (unexposed section) and forehead (exposed section).

Figure 14:
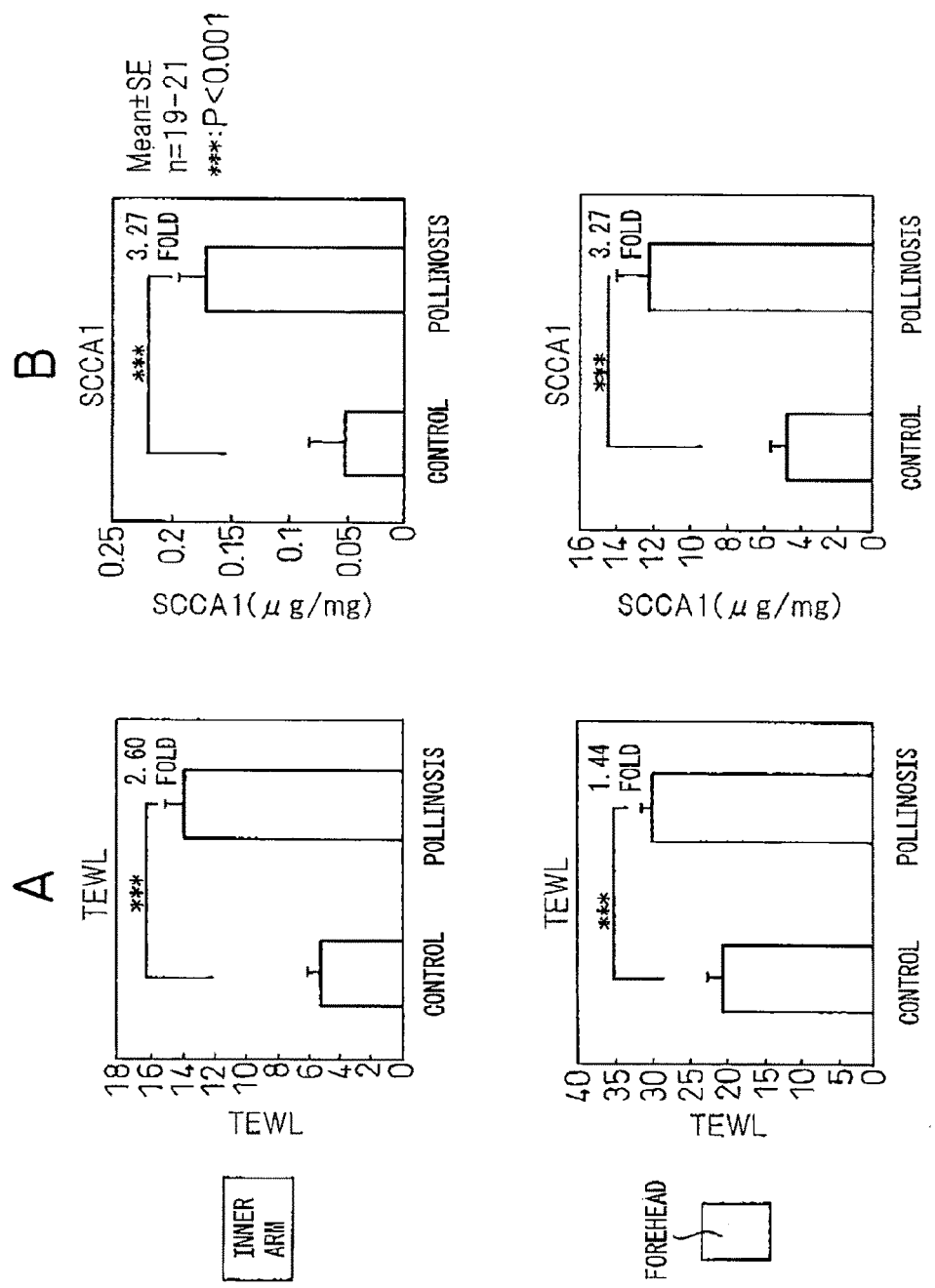
FIGS. 14A-14B show the correlation between roughening and SCCA-1 amount in pollen hypersensitive skin, as provided by TEWL (FIG. 14A) and with SCCA-1 expression (FIG. 14B).
Figure 15:
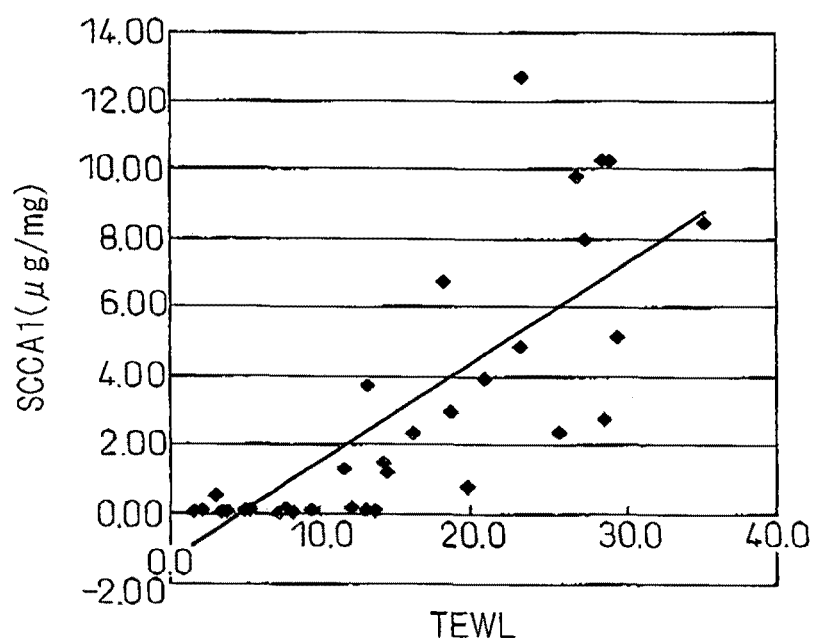
FIG. 15 shows the correlation between roughening and elevated SCCA-1 expression in pollen hypersensitive skin.

FIG. 14 shows the correlation of rough pollen hypersensitive skin with TEWL (A), and with SCCA-1 expression (B). As the graphs clearly show, pollen hypersensitivity exhibited a significant increase in TEWL and a reduced skin barrier function, while rough skin had notably increased expression of SCCA-1 compared to healthy individuals. Thus, SCCA-1 was clearly shown to be a marker for skin roughness due to pollen hypersensitivity. Moreover, in pollen hypersensitive skin, increased TEWL, i.e. reduced barrier function, was also found in the inner arm which is not exposed to light, thus suggesting that systemic inflammatory response and increased SCCA impairs the barrier function of the body. FIG. 15 shows the correlation between rough skin and augmented SCCA-1 expression for pollen hypersensitive skin. The Pearson correlation coefficient was 0.8086 for SCCA-1 and TEWL, which was a significant correlation. Thus, it was shown that SCCA-1 expression increases with reduced skin barrier function, i.e. worsening skin roughness, due to pollen hypersensitivity.

Consequently, SCCA can be used as a marker to judge susceptibility to pollen hypersensitivity-associated skin roughness even before symptoms of skin roughness appear, thus allowing prevention and early treatment (for example, before onset). Furthermore, the discovery of parakeratosis in pollen hypersensitive skin is completely new, and the fact that barrier function impairment and parakeratosis in pollen hypersensitive skin is associated with SCCA is of great interest.

What is claimed is:

1. A method for judging susceptibilities of an individual to skin roughening caused by pollen hypersensitivity, comprising: quantitatively measuring an amount of squamous cell carcinoma antigen (SCCA) expression in skin stratum corneum cells of said individual and judging susceptibilities of said individual to the skin roughening based on an increased level of SCCA compared to normal skin, wherein the increased level of SCCA indicates that the individual is susceptible to skin roughening, and wherein the skin stratum corneum cells are obtained by tape stripping.

2. The method according to claim 1, wherein the amount of SCCA expression is measured by enzyme-linked immunosorbent assay (ELISA) using antibody specific for SCCA.

3. The method according to claim 1, wherein the SCCA is SCCA-1.

4. The method of claim 1, further comprising indicating susceptibility of said individual to a user.

5. A method for judging susceptibilities of an individual to skin aging due to ultraviolet irradiation exposure, comprising: quantitatively measuring an amount of squamous cell carcinoma antigen (SCCA) expression in skin stratum corneum cells of said individual and judging susceptibilities of said individual to the skin aging based on an increased level of SCCA compared to normal skin, wherein the increased level of SCCA indicates that the individual is susceptible to skin aging, and wherein the skin stratum corneum cells are obtained by tape stripping.

6. The method according to claim 5, wherein the amount of SCCA expression is measured by enzyme-linked immunosorbent assay (ELISA) using antibody specific for SCCA.

7. The method according to claim 5, wherein the SCCA is SCCA-1.

8. The method of claim 5, further comprising indicating susceptibility of said individual to a user.

* * * * *

SEQUENCE LISTING

<160> NUMBER OF SEQ ID NOS: 12

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
aaggatccaa tccgcggtct tggaagagg ag                                      32

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
tttctgcagg ttgcagatac agccgtttcc ggagggtgc                              39

<210> SEQ ID NO 3
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 3

Tyr Val Ala Asp
 1

<210> SEQ ID NO 4
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 4

Val Asp Val Ala Asp
 1               5

<210> SEQ ID NO 5
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 5

Asp Glu Val Asp
 1

<210> SEQ ID NO 6
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 6

Val Glu Ile Asp
 1

```
-continued

<210> SEQ ID NO 7
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 7

Ile Glu Thr Asp
 1

<210> SEQ ID NO 8
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 8

Leu Glu His Asp
 1

<210> SEQ ID NO 9
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 9

Asp Asn Leu Asp
 1

<210> SEQ ID NO 10
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 10

Trp Glu His Asp
 1

<210> SEQ ID NO 11
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 11

Lys Asp Ser Pro Gln
 1               5

<210> SEQ ID NO 12
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 12

Thr Val Gly Gly Asp
 1               5
```